(12) United States Patent
Cosman

(10) Patent No.: US 7,077,842 B1
(45) Date of Patent: Jul. 18, 2006

(54) OVER-THE-WIRE HIGH FREQUENCY ELECTRODE

(76) Inventor: Eric R. Cosman, 872 Concord Ave., Belmont, MA (US) 02478-0002

( * ) Notice: Subject to any disclaimer, the term of this patent is extended or adjusted under 35 U.S.C. 154(b) by 7 days.

(21) Appl. No.: 10/058,967

(22) Filed: Jan. 30, 2002

Related U.S. Application Data

(60) Provisional application No. 60/310,438, filed on Aug. 3, 2001.

(51) Int. Cl.
*A61B 18/18* (2006.01)

(52) U.S. Cl. .......................................... 606/41; 128/898

(58) Field of Classification Search ............ 606/27–52; 128/898
See application file for complete search history.

(56) References Cited

U.S. PATENT DOCUMENTS

| 4,483,338 | A |   | 11/1984 | Bloom et al. |
|-----------|---|---|---------|--------------|
| 4,682,596 | A |   | 7/1987  | Bales et al. |
| 4,936,281 | A |   | 6/1990  | Stasz |
| 4,998,933 | A |   | 3/1991  | Eggers et al. |
| 5,178,620 | A |   | 1/1993  | Eggers et al. |
| 5,348,554 | A |   | 9/1994  | Imran et al. |
| 5,454,809 | A |   | 10/1995 | Janssen |
| 5,500,012 | A | * | 3/1996  | Brucker et al. ............. 607/122 |
| 5,520,684 | A |   | 5/1996  | Imran |
| 5,545,161 | A |   | 8/1996  | Imran |
| 5,658,278 | A |   | 8/1997  | Imran et al. |
| 5,688,267 | A | * | 11/1997 | Panescu et al. ............... 606/41 |
| 5,782,760 | A | * | 7/1998  | Schaer ...................... 600/381 |
| 5,951,546 | A |   | 9/1999  | Lorentzen |
| 6,241,702 | B1 |  | 6/2001  | Lundquist et al. |
| 6,506,189 | B1 | * | 1/2003 | Rittman et al. ............... 606/41 |

FOREIGN PATENT DOCUMENTS

| WO | WO 96/18349 | 6/1996 |
| WO | WO 96/34571 | 11/1996 |

OTHER PUBLICATIONS

Cosman, et al., "Theoretical Aspects of Radiofrequency Lesions in the Dorsal Root Entry Zone", Neurosurgery, vol. 15, No. 6, pp. 945-950, (1984).
Gervais, et al., "Radio-frequency Ablation of Renal Cell Carcinoma: Early Clinical Experience", Radiology, vol. 217, No. 3, pp. 665-672, (2000).

(Continued)

*Primary Examiner*—Roy D. Gibson
*Assistant Examiner*—Pete Vrettakos
(74) *Attorney, Agent, or Firm*—Steptoe & Johnson LLP

(57) ABSTRACT

A device for ablation of target tissue in the living body such as a tumor comprises an elongate member that can be guided over a guide element into the target tissue. The elongated element has an electrode at its distal portion. The electrode is configured to be energized with high frequency energy to ablate the target tissue. The elongate member has a guide hole through it and is configured to pass over a guide element that has perforated and penetrated the skin and tissue along a tract to the target volume. The elongate member can be made of a rigid metal tube or a flexible plastic tube. The elongate member can include a cooling channel within it so that cooling fluid can be circulated within the elongate member to cool the electrode, and thus to enlarge the ablation volume at the target tissue.

24 Claims, 12 Drawing Sheets

OTHER PUBLICATIONS

Goldberg, et al., "Tissue Ablation with Radiofrequency: Effect of Probe Size, Gauge, Duration, and Temperature on Lesion Volume", Acad. Radiol., vol. 2, No. 5, pp. 399-404, (1995).

Goldberg, et al., "Thermal Ablation Therapy for Focal Malignancy; a Unified Approach to Underlying Principles, Techniques, and Diagnostic Imaging Guidance", AJR, vol. 174, pp. 323-331, (2000).

* cited by examiner

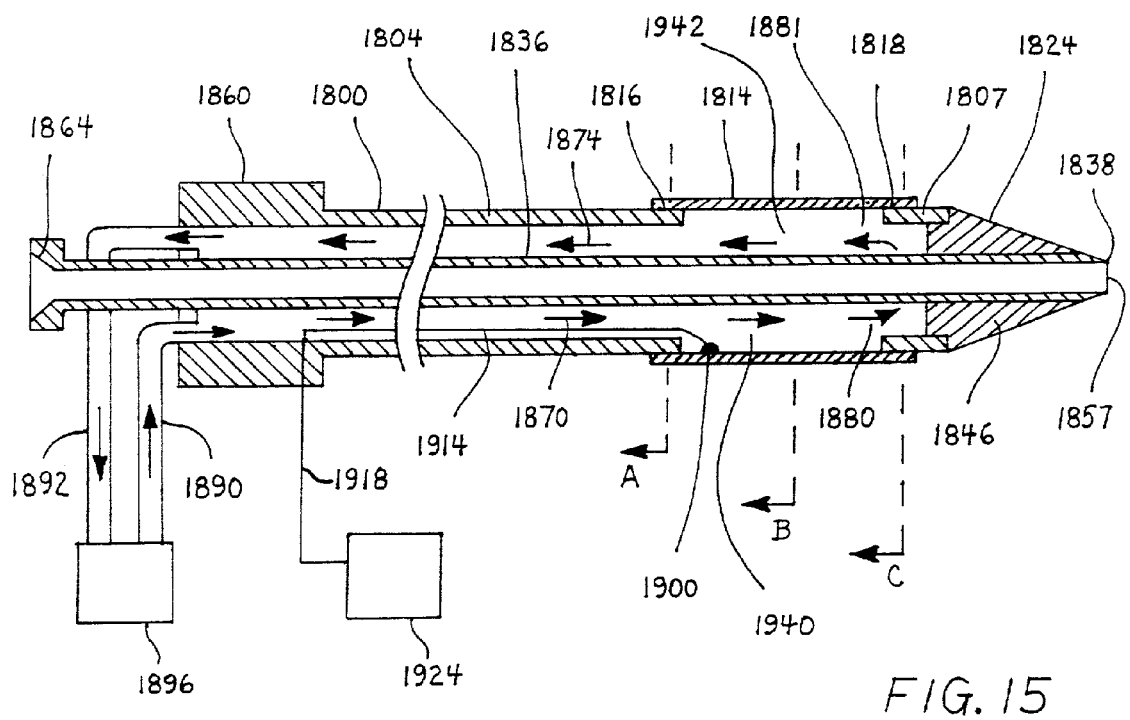
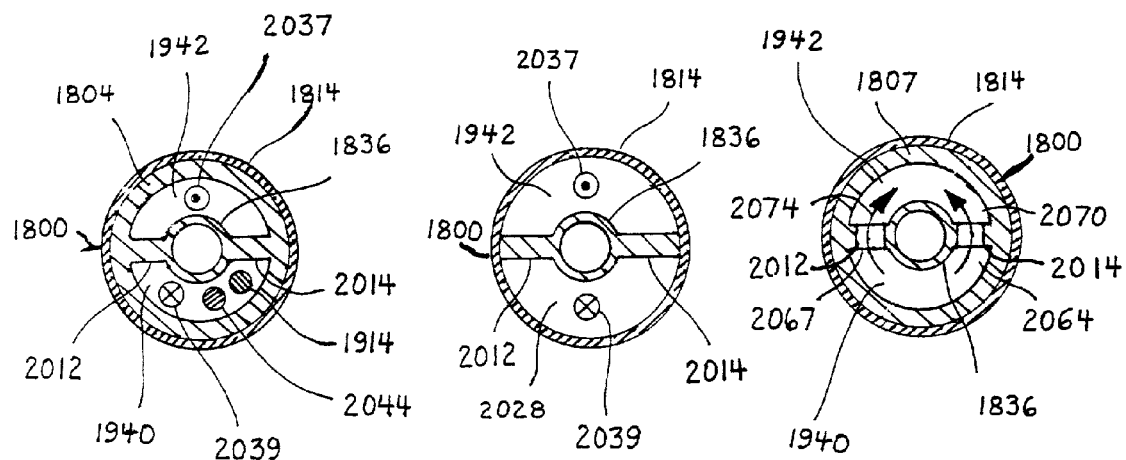
FIG. 15
FIG. 16A   FIG. 16B   FIG. 16C

OVER-THE-WIRE HIGH FREQUENCY ELECTRODE

CLAIM OF PRIORITY

This application claims priority to U.S. patent application Ser. No. 60/310,438, filed on Aug. 3, 2001, the entire contents of which are hereby incorporated by reference.

TECHNICAL FIELD

This invention relates generally to the advances in medical systems and procedures for prolonging and improving human life. More particularly, this invention relates to an improved method and system involving a high frequency electrode that is inserted into the human body over a guide wire for performing thermal high frequency ablation of target tissue such as cancerous tumors.

BACKGROUND

The use of high frequency electrodes for heat ablation treatment of functional disease and in the destruction of tumors is well known. One example is the destruction of cancerous tumors of the kidney using radio frequency (RF) heat ablation. A paper by D. W. Gervais, et al., entitled "Radio-frequency Ablation of Renal Cell Carcinoma: Early Clinical Experience," Radiology, vol. 217, no. 2, pp. 665–672 (2000) describes using a rigid tissue perforating and penetrating electrode that has a sharpened tip to self-penetrate the skin and tissue of the patient. This paper is hereby incorporated by reference herein in its entirety. The exposed conductive tip of the electrode is placed in the tumor within the kidney. The electrode has cooling fluid circulating within it to enable larger ablation volumes to be made. Such rigid, cooled, tissue-perforating radio frequency electrodes are available from Radionics, Inc., Burlington, Mass.

The theory behind and practice of RF heat ablation has been known for decades and a wide range of suitable RF generators and electrodes exists. For example, equipment for causing heat lesions is available from Radionics, Inc., located in Burlington, Mass. A research paper by E. R. Cosman, et al., entitled "Theoretical Aspects of Radiofrequency Lesions in the Dorsal Root Entry Zone," Neurosurgery, Vol. 15, No. 6, pp. 945–950 (1984) describes various techniques associated with radio frequency lesions and is hereby incorporated by reference herein in its entirety. Also, research papers by S. N. Goldberg, et al., entitled "Tissue Ablation with Radio Frequency: Effect of Probe Size, Gauge, Duration, and Temperature on Lesion Volume," Acad. Radiol., Vol. 2, pp. 399–404 (1995), and "Thermal Ablation Therapy for Focal Malignancy," AJR, Vol. 174, pp. 323–331 (1999) describe techniques and considerations relating to tissue ablation with radio frequency energy and are hereby incorporated by reference herein in its entirety.

SUMMARY

In one aspect, a device for ablating tissue in the living body includes an elongate member defining a longitudinal passage having a distal opening and a proximal opening dimensioned to pass a guide element. The elongate member includes an electrode disposed at a distal portion of the elongate member and configured to be energized with high frequency energy to ablate tissue.

In another aspect, a device for ablating tissue includes a rigid elongate tubular member defining a longitudinally extending lumen having a distal opening and a proximal opening. The lumen is dimensioned to pass along a guide element. A distal portion of the tubular member has a blunt distal tip. The device also includes an electrode disposed at a distal portion of the tubular member and configured to be energized with high frequency energy to thermally ablate tissue, and a fluid channel defined within the tubular member, the fluid channel in fluid communication with the fluid input port and the fluid output port and in thermal communication with the electrode.

In another aspect, a device for ablating tissue includes a flexible elongate tubular member defining a longitudinally extending lumen having a distal opening and a proximal opening. The lumen is dimensioned to pass along a guide element. A distal portion of the tubular member has a blunt distal tip. The device also includes an electrode disposed at a distal portion of the tubular member and configured to be energized with high frequency energy to thermally ablate tissue, and a fluid channel defined within the tubular member, the fluid channel in fluid communication with the fluid input port and the fluid output port and in thermal communication with the electrode.

In another aspect, a system for ablation of a tissue in the living body includes a guide element and an ablation system. The ablation system includes an elongate member defining a longitudinal channel having a distal opening and proximal opening, the elongate member being dimensioned to slide along the guide element. The ablation system also includes an electrode at a distal portion of the elongate member and configured to be energized with high frequency energy to ablate the tissue. The system can also include a needle element defining a longitudinal lumen dimensioned to pass the guide element. The needle can include a sharp distal tip configured to perforate the tissue. The elongate member can define a fluid channel in fluid communication with a fluid input and a fluid outlet and in thermal communication with the electrode. The ablation system can also include a high frequency generator, electrical conductors connecting the high frequency generator to the electrode, a fluid agent injector, or a coolant supply connected to a fluid input of the elongate member.

The elongate member can be rigid or flexible. The elongate member can include a blunt distal tip. The blunt distal tip can converge smoothly with the distal opening. The blunt distal tip can include a rounded contour surrounding the distal opening. The blunt distal tip can include a tapered contour converging with the distal opening. The blunt distal tip can include a fluid sealed junction between the metal tube and the inner metal tube.

The device can include a fluid inlet port and a fluid outlet port. The elongate member can further define a fluid channel in fluid communication with the fluid inlet port and the fluid outlet port. The fluid channel can be in thermal communication with the electrode.

The electrode can include an exposed portion of the external surface of the outer metal tube. The electrode can include a metal element. The electrode can be a ring. The electrode can include a tapered contour converging with the distal opening.

The tubular member can include a metal tube having an external surface and an electrical insulator configured to electrically insulate a portion of the external surface of the metal tube. The tubular member can include a plastic tube. The device can include an inner metal tube disposed within the metal tube and defining a portion of the lumen. The fluid channel can be located at least in part between the metal tube and the inner metal tube.

The guide element can include a flexible guide wire or a rigid stylet wire. The guide element comprises an anchor that extends laterally from a distal guide portion of the guide element. The anchor can be configured to anchor the distal guide portion near a target. The guide element can include a tube containing a movable member. The movable member can be a tube or an anchor.

In another aspect, a method for thermal ablation of a target volume includes perforating and penetrating a living body using a guide element to establish a tract through the body to the target volume, sliding an electrode along the guide element to position the electrode near the target volume, connecting the electrical connection to a high frequency generator, and supplying high frequency energy from the generator through the electrode to the target volume to thermally ablate the target volume. The electrode includes an elongate member defining a longitudinal passage dimensioned to pass along the guide wire, a conductive surface at a distal portion of the elongate member, and an electrical connection between the conductive surface and a proximal portion of the elongate member.

The method can also include cooling the electrode while supplying high frequency energy to change a spatial distribution of heat near the electrode. Cooling can include connecting a source of a coolant to a fluid input and causing a coolant to flow in a fluid channel in the elongate member. The fluid channel can be fluid communication with the fluid input and a fluid output and in thermal communication with the electrode. Perforating and penetrating can include passing a sharp needle through skin and tissue. Positioning can include passing the guide wire through the needle and removing the needle over the guide wire to leave the guide wire in the tract. Positioning can include deploying an anchor from the guide wire to anchor the guide wire in the tract. The method can also include dilating the tissue along the tract after positioning the guide wire by passing a dilating element over the guide wire to expand the tissue along the tract prior to sliding the electrode along the guide wire.

In certain circumstances, the method can include introducing a fluid agent through the guide element. For example, the method can include introducing a chemotherapeutic agent through the guide element prior to or while supplying high frequency energy. The chemotherapeutic agent can act in combination with the step of supplying high frequency energy to enlarge the volume of ablation.

Advantages of the device can include its use in minimally invasive ablation techniques with better guidance and with less trauma to tissue. A guide wire or stylet that punctures and perforates tissue can have a small diameter, producing less trauma and making device placement easier. Guide wire placements using needles are well known to radiologists and are well adapted to image-guided techniques. Guide wires can be placed in any deep organ or any tissue type without displacing the organ or losing target position. Guide wires can also be configured to anchor to target tissue and hold the device in position at the target despite body organ movement.

A guide wire-guided RF electrode need not itself perforate, cut, or puncture skin or tissue. A guide wire-guided RF electrode can include a blunt distal tip that gently expands and dilates tissue without cutting when the electrode slides over the guide wire. Gentle expansion and dilation of tissue reduces risk of bleeding, since tissue is laterally and frontally compressed during the process, which can be advantageous in vascular target sites such as the kidney where the risk of ripping critical blood vessels is reduced by a dull or rounded electrode tip.

An electrode with a guidance channel through it also allows agents, such as anesthetics, saline loaded fluids, gels, or chemotherapeutic agents, to be injected through the channel to the target site to ease device insertion or enlarge the ablation volume.

The invention can be used in numerous organs in the body, including the brain, spine, liver, lung, bone, kidney, abdominal structures, etc., and for the treatment of cancerous tumors, functional disorders, pain, tissue modifications, bone and cartilage fusions, and in cardiac ablation.

The details of one or more embodiments of the invention are set forth in the accompanying drawings and the description below. Other features, objects, and advantages of the invention will be apparent from the description and drawings, and from the claims.

DESCRIPTION OF DRAWINGS

In the drawings which constitute a part of the specification, embodiments exhibiting various forms and features hereof are set forth, specifically:

FIG. 15 is a schematic diagram showing a guide element-directed electrode with a flexible shaft member, a metal ring electrode, and conical distal tip;

FIG. 16A is a schematic diagram showing a sectional view at line A of FIG. 15;

FIG. 16B is a schematic diagram showing a sectional view at line B of FIG. 15;

FIG. 16C is a schematic diagram showing a sectional view at line C of FIG. 15;

Like reference symbols in the various drawings indicate like elements.

DETAILED DESCRIPTION

Figure 1A:
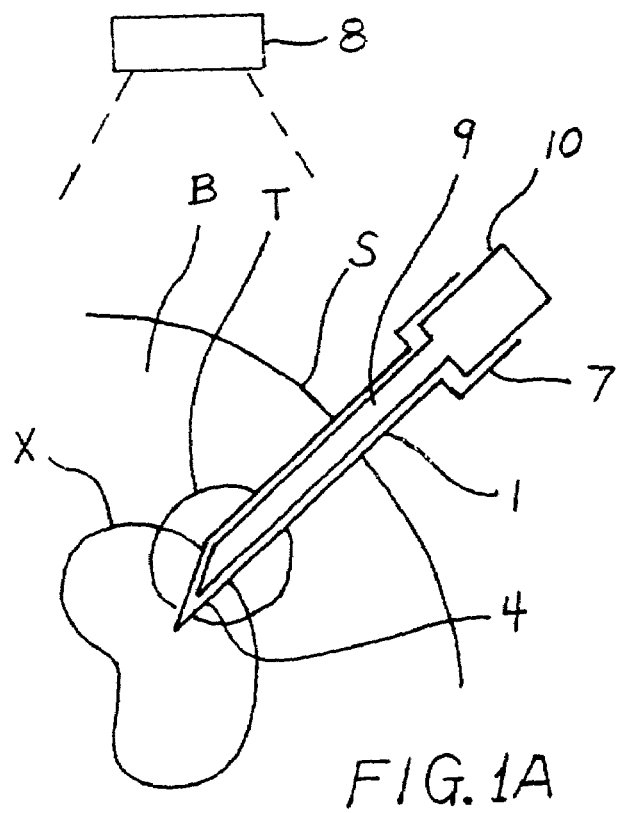
FIG. 1A is a schematic diagram showing percutaneous placement of a guide needle into a target tissue of a patient's body.
Figure 1B:
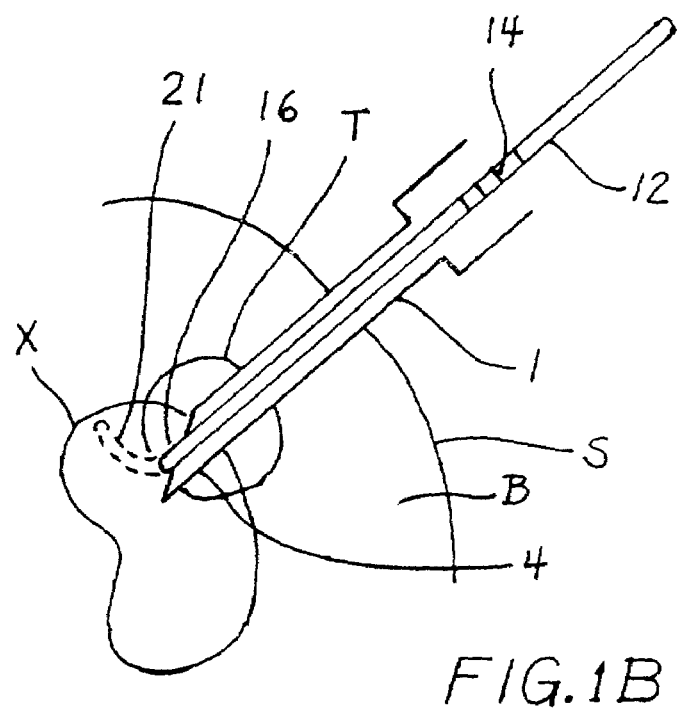
FIG. 1B is a schematic diagram showing placement of a guide element through a percutaneously placed needle.
Figure 1C:
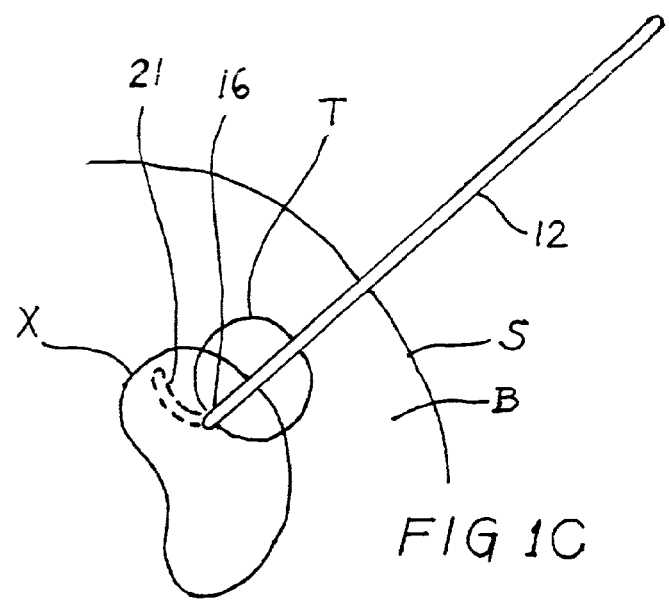
FIG. 1C is a schematic diagram showing removal of a guide needle, leaving a guide element in place near a target tissue.
Figure 1D:
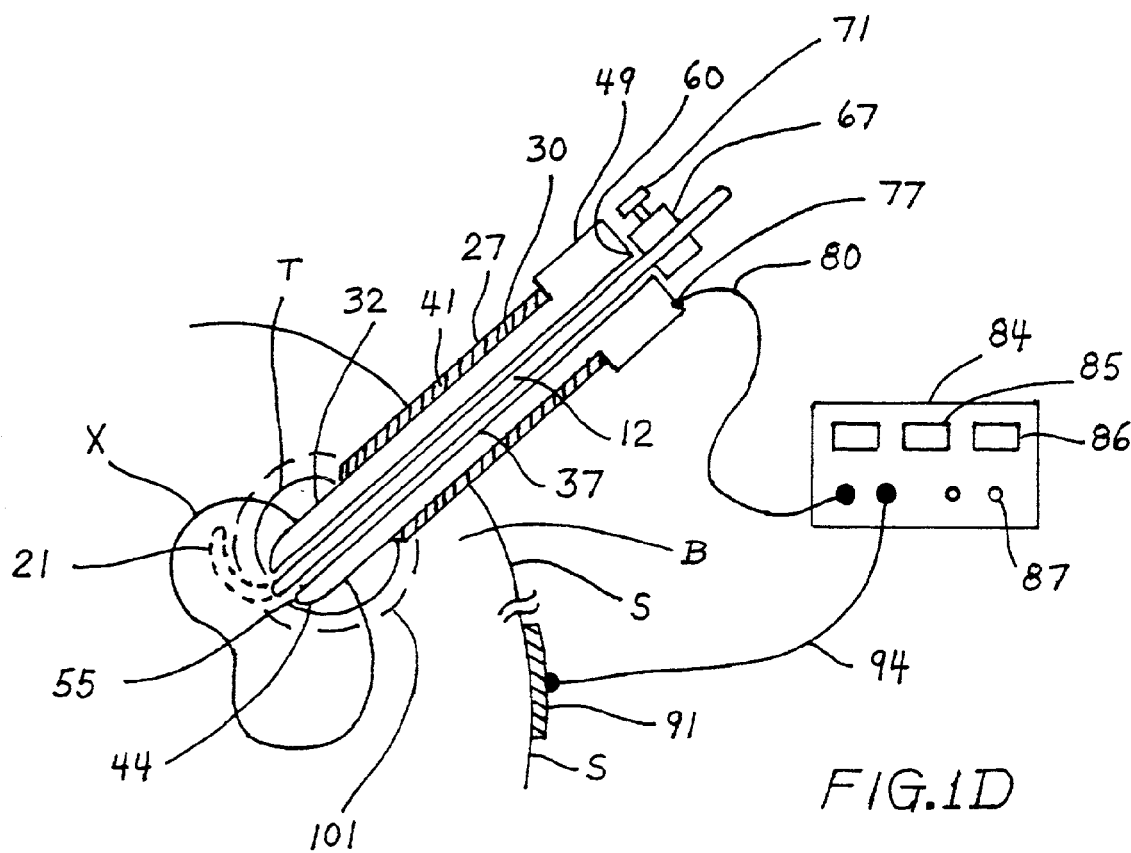
FIG. 1D is a schematic diagram showing guidance of a guide element-directed electrode to a target tissue by a guide element and connection to a high frequency generator.

Referring to FIG. 1D, a guide element-directed electrode such as high frequency probe 27 includes a lumen 37 for directing elongate member 30 over a guide element 12, e.g., a guide wire, to a target tissue or surgical site. The member includes a blunt, non-tissue penetrating distal end 44. Coupled to the member is an electrode, e.g., an exposed distal tip 32 of the member, which is energized with high frequency energy to treat the target tissue. A majority of member 28 is coated with an insulating layer 41, such that only the exposed distal tip 32 serves as the electrode.

Referring to FIG. 1A, in use, a needle 1 is inserted into tissue B of a living body and through the skin S, and into an operable field within the patient's body, which can include an organ X and a target site T. For example, the organ X can be the kidney, prostate, bladder, liver, lung, brain, or any other organ within the body. The target tissue T can be, for example, a cancerous tumor or other functionally diseased tissue that is within the organ X, on its surface, or nearby. The insertion of needle 1 can take place, for example, under image-guided control with an imaging machine 8, such as X-ray, CT, MRI, angiograph, or ultrasound. If desired, an obdurating stylet 9 can be positioned in needle 1 during introduction into the tissue to occlude pointed tip 4 of needle 1. The needle and stylet have respective hubs 7, 10, which can lock and register to each other.

Referring to FIG. 1B, once needle 1 has been properly placed into body B, the stylet 9 is removed and a guide wire or a guide stylet 12 is inserted through the needle 1. The needle 1 used to perforate and penetrate the skin S and tissue T, as well as that of the target site T and organ X can be rigid and can form a tract that guides the guide wire 12 into its proper location at target T. The guide wire or guide stylet 12 can be thin and flexible, semi-rigid, or very rigid. The straight tip 16 of the guide wire 12 can be positioned proximate the pointed tip 4 of the needle 1, as indicated by markings 14 on the guide wire 12. Alternatively, the guide wire 12 can have a flexible curved tip 21 that emerges from the needle tip 4 so as to anchor the guide wire 12 within the organ site X at target tissue T. Anchoring reduces movement or slippage of the guide wire due to organ or body movement, such as during respiration, thereby stabilizing the guide wire in position at the target T.

Referring to FIG. 1C, the needle (not shown) is then removed, leaving the guide wire 12 within the bodily tissue B and its straight tip 16 or, alternatively, curved tip 21, properly placed within organ X and contacting target tissue T, or nearby tissue. The guide wire or guide stylet 12 can be thin and flexible, semi-rigid, or very rigid. When the needle is removed, an access tract, as represented by the guide wire 12, is left in its in place.

Referring to FIG. 1D, high frequency probe 27 is then slid over guide element 12. Elongate member 30 can be a rigid, metal tube. Alternatively, elongate member 30 can be semi-rigid, such as a plastic tube, or flexible, as in a rubber or flexible plastic catheter. Through channel lumen 37 extends from distal tip end 44 to the proximal end at hub 49. The through channel lumen 37 opens through the surface of the electrode at distal tip end 44 at a distal opening 55, and at the proximal end at a proximal opening 60. A depth stop or clamping device 67 anchors the position of guide element 12 to the probe 27 using a lock element 71 on depth stop 67 that secures the depth stop to the shaft of guide element 12.

When inserted through skin S into bodily tissue B, probe 27 is guided along the tract established by guide element 12. As it moves through the bodily tissue B towards target tissue T or organ X, the tip 44 moves along the tract established by the entry of needle into bodily tissue B and of guide element 12. Guide element 12 occludes the distal opening 55 of probe 27 during the movement of distal tip end 44 through the bodily tissue B, preventing tissue from embedding and impacting in the channel lumen 37. The tip 44 can be shaped in a smooth and rounded form so that it does not cut or perforate the bodily tissue B as it slides along guide wire 12. As the probe 27 follows the tract made by the needle and guide element 12 and moves deeper into bodily tissue B, a taper at the distal tip end 44 can dilate the surrounding tissue. Alternatively, a separate dilator element can be used over guide element 12 prior to passage of probe 27, in which case probe 27 does not dilate the tissue at all but merely follows a preformed expanded tissue tract.

The exposed distal tip 32 is conductive and can be connected by electrical connections (not shown) in the elongate member 30 to a connection 77 at the hub 49. Connection 77 can be joined by connector 80 to a high frequency generator 84. Generator 84 is a source of high frequency electrical voltage or current applied through connector 80 and member 30 to the exposed tip 32. This induces electrical current to flow through the body tissue B. In the example shown in FIG. 1D, the current is returned to the generator 84 by a reference electrode 91, which can be, for example, a large surface area electrode in electrical contact with skin S through return connector 94 at an appropriate portion of the patient's body. Such a monopolar electrode configuration can result in relatively high current densities in the region of target tissue T near the exposed tip 32. The high frequency current within the target tissue T deposits energy in the surrounding tissue and the electrode due to Joule heating of the tissue. Tissue heated to greater than approximately 50° C. for several minutes kills the cells and disrupts other constituent matter of the tissue. When tip 32 is not cooled, the temperature falls off in space away from the region near tip 32 and forms an ablation zone within which the tissue reaches a temperature greater than 50° C. The isotherm associated with the ablation zone is illustrated by the dashed curve 101. The ablation zone 101 can engulf the entire target tissue T if target tissue T is, for example, a cancerous tumor or functionally diseased region. Alternatively, if the tip 32 is cooled by flowing a fluid within the tip from an external source, as described below, the temperature distribution around a cooled tip 32 initially increases moving away from the tip 32 and reaches a maximum at some distance from the tip 32, thus producing an enlarged ablation zone relative to the ablation zone 101.

Guide element 12 with curved tip 21, or multiple curved hooks or prongs (not shown), which anchor the tip to tissue, helps limit movement of the guide element tip 21 during manipulation, e.g., as the probe 27 slides over the guide element 12. Thus the tip 32, on approaching the curved tip 21, can be in the predetermined anchored position near target tissue T. Further, with clamp 67 in place, movement of the target tissue T, such as with respiration or with further manipulation, will also move the probe 27 and anchored guide element 12 along with the tissue T such that the tip 32 remains in proper position relative to target T. For example, where the organ X is the kidney and target tissue T is a renal cell carcinoma, the insertion of probe 27 can tend to displace the organ because the organ has a tough cortex. By anchoring the guide element 12 with an anchoring mechanism, such as curved tip 21, movement of the guide element relative to the target tissue T can be reduced and error in placement of the ablation volume can be diminished.

The generator 84 can have many control and readout functions associated with RF parameters of the ablation process, as illustrated by meters 85 and 86, which can display output power, current, voltage, impedance, or other parameters of the heating process. Controls 87 which are used to carry out the ablation process can be, for example, manual, automatic, or computer controlled to govern and monitor the process and display of the generator. Ablation time, duration, and set points can be displayed. The generator 84 can be, for example, a high frequency generator with various possible frequency ranges including: several tens of kilohertz to 100 kilohertz; 100 kilohertz to 1 megahertz; 1 megahertz to several megahertz; several hundred megahertz; or greater frequencies. Radio frequencies in the 100 kilohertz to 100 megahertz can be effective in tissue ablation. Connector 80 can have, for example, multiple connections, and can connect, for example, individually to tip 32 or, if further independent electrode surfaces are present on probe 27, connector 80 can connect to each electrode surface individually. In a bipolar configuration (not shown), where probe 27 has multiple conductive independently connected electrode surfaces, the return connector 94 can be connected through the hub 49 to one or more of the electrode surfaces, and the connector 80 can be connected to other of the electrode surfaces to produce a bipolar current pattern in the target tissue to create desired heating patterns. Generator 84 can have a supply power in the range from 0 to 10 watts, 0 to 50 watts, 0 to 200 watts, 0 to 400 watts, or more. If desired, probe 27 can include temperature sensors (not shown) such as one or more thermocouple sensors built into the tip 32. The temperature sensor can be connected by separate wires to the generator 84, and the measured temperature can be displayed on display 85. The time duration of heat ablation can vary with the circumstances of the procedure. For example, the time duration of heat ablation can be in the range of 0 to 1 minute, 0 to 3 minutes, 0 to 10 minutes, 0 to 60 minutes, or longer.

Figure 2:
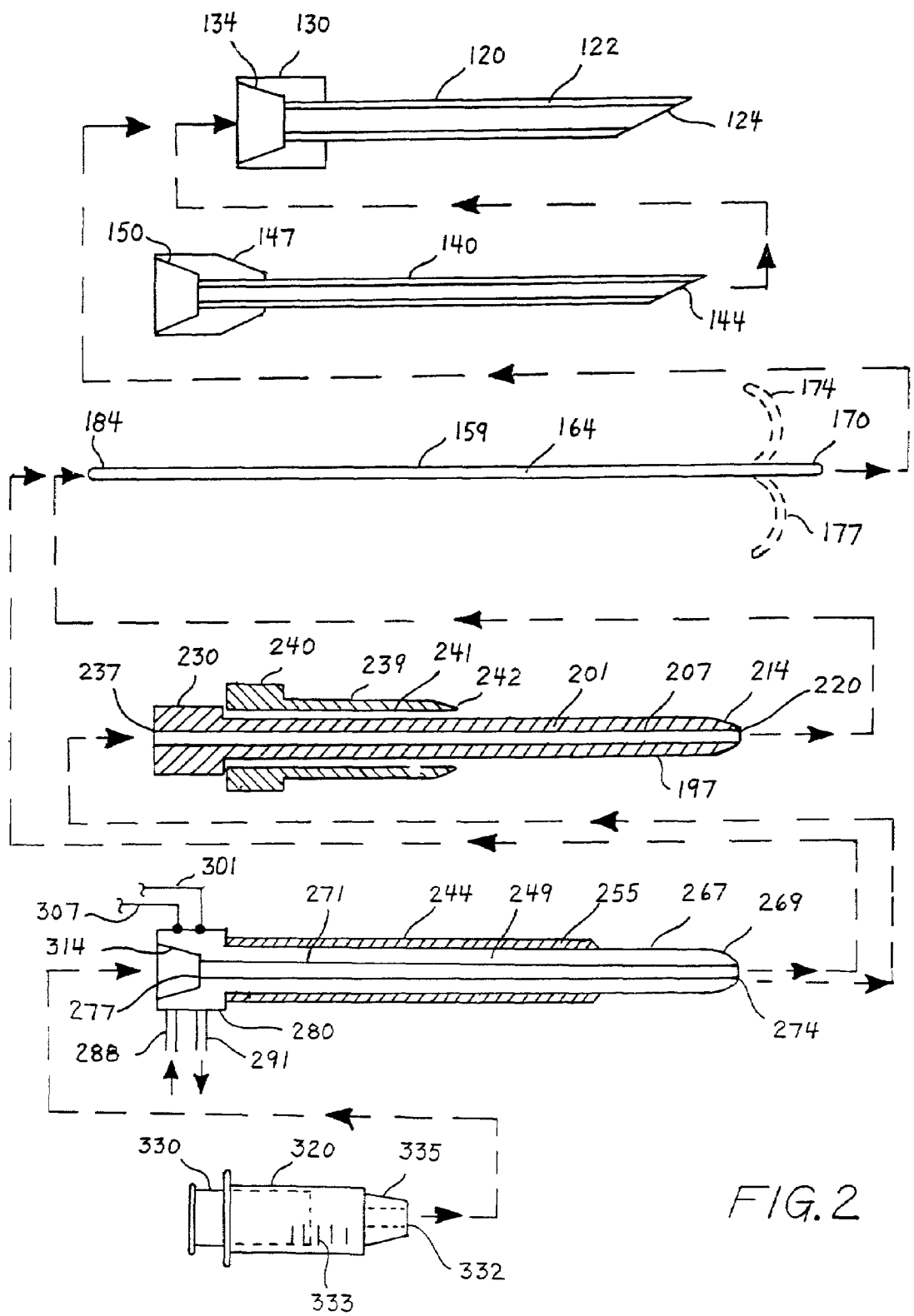
FIG. 2 is a schematic diagram showing a system of needles, guide elements, dilators, a guide element-directed electrode, and an injector.

Referring to FIG. 2, sectional views of a system of elements is shown for introducing a probe 244. The dashed lines with arrows indicate sequential insertions or connections of one element to another that can be made in this system. A guide needle 120 has a tubular shaft 122 with a distal end 124. Needle 120 is used to perforate and penetrate the skin and body tissues to establish a hole directed towards the target tissue. Needle 120 is introduced into the body, for example, using an obdurating stylet (not shown) similar to that described in FIG. 1A. Needle 120 can be made of a variety of materials, including a metal or a hard plastic. Needle 120 includes a hub 130 at its proximal end. Hub 130 has a luer taper 134. Hub 130 can be made of metal or plastic to suit imaging compatibility. The needle can be introduced into the body, for example, under image guidance and can be made from a material or combination of materials, for example, a metal or a metal alloy, compatible with CT, MRI, or X-ray imaging. Distal end 124 can have an angular bevel capable of puncturing tissue, as shown. Alternatively, distal end 124 can have a squared-off shape and the obdurating stylet (not shown) can have a point such as a conical or a trocar point, which enables puncture, perforation, and penetration of the needle through skin and tough tissue. When using a metal obdurating stylet, needle 120 can have a plastic shaft 122.

Once needle 120 is introduced into the body, the obdurating stylet, if used, can be removed, and an ancillary needle 140 can be inserted to introduce fluid agents or to perform a biopsy. Ancillary needle 140 includes a distal tip 144, which can be beveled, as shown. Alternate tips, such as side-cutting devices, can be used for biopsy. Ancillary needle 140 also includes a hub 147 that can be shaped to fit with the luer 134 of needle 120 to perform aspirations or provide a fluid-tight seal. Agents such as saline, hypertonic saline, saline gel, alcohol, a chemotherapeutic agent, or other agents can be injected by connecting luer lock 150 on the hub 147 to a syringe to treat the target tissue, for example, so as to enhance the size of the ablation volume made with the RF electrode. For example, injection of hypertonic saline or hypertonic saline gel can produce an effectively larger conductive electrode region, thereby enabling larger heat lesion volumes to be made when the electrode is introduced and used to ablate tissue.

A guide element 159 can be introduced into guide needle 120 once after the stylet (not shown) or ancillary element 140 has been removed. The guide element 159 includes a distal end 170 and a proximal end 184. The guide element can be, for example, a flexible guide wire, such as a well-known Seldinger wire, which includes a helically wound wire structure and an inner concentric wire. The helical structure and concentric wire can be welded together at the distal end 170 and the proximal end 184. Such a helically wound guide wire can have excellent lateral flexibility and very little longitudinal stretch. Other types of guide elements can be similar to a Seldinger wire but can have a permanent curve or arc at the distal end, as indicated by the curved, dashed lines 174 or 177. The curved portions 174 or 177 can include a flexible wire element or multiple wire elements introduced into the guide needle 120 so that when distal end 124 emerges from the needle, the flexible wire element or elements assume an arced or curved path. The curve or arc can secure the guide element in target tissue, as described above. Alternatively, the guide element 159 can be a relatively stiff stylet such as a solid stainless steel wire or a bundle of multiple wire stylets or tubes, or the stylet can be formed from flexible metal, such as nitinol, where the curved ends 174 and 177 form from a memory of the metal and can be pushed into the tissue laterally once emerging from the guide needle 120 to provide a strong anchor. The guide wire can be rotated around its axis such that a single curved end, such as 174, can be rotated azimuthally and thus be directed in the direction as indicated by curve 177, depending on the target region encountered. The guide wire can have a blunt or sharp point to suit the toughness or the delicacy of tissues encountered. When encountering tough target tissue, such as cartilage, cortexes of organs such as the kidney, or bone, guide needle 120 can be firmly pushed into the target, the stylet can be removed, and a stiff guide element 159 can be pushed into place and anchored at the target. The guide element can be electrically insulated, for example, with a non-conductive coating, so that it will not influence the magnitude and direction of current flow during high frequency ablative heating when the electrode is introduced and used to ablate tissue.

Once guide element 159 is in place, needle 120 is removed from the patient's body, leaving the guide element 159 in place in the tissue. In some cases, further dilation of the body tissue along the guide element tract is desired. If so, dilation element 197 can be passed over guide element 159 to make a wider tract. Dilation element 197 has an elongated body 201 with a dilating tip 214. Dilation element 197 has a traversing longitudinal channel 207 which opens at its distal end with opening 220. At the proximal end, dilation element 197 has a hub 230 including proximal opening 237 to channel 207. Dilation element 197 can be made of a metal, a plastic, a hard silicone, or other appropriate material. Dilation element 197 can be rigid, semi-rigid, or flexible. If lateral dilation of the tissue tract along guide element 159 needs to be incremented in fractions of a millimeter or in millimeters, then more than one dilation element similar to dilation element 197 can be passed sequentially over guide element 159, or multiple dilation elements can telescope over each other to expand the tract diameter. The distal tip 214 can be smooth, conical, bullet-shaped, or septum-shaped. The distal tip 214 can be substantially free of sharp points or edges to gently expand tissue laterally as the shaft 201 is pushed inward without cutting or piercing the tissue along the tract. If desired, a sheath or cannula 239 can cover dilation element 197 when dilation element 197 is passed over guide element 159. The sheath includes an inner lumen 241 and tip 242, and a hub 240 that can abut or lock with hub 130 during dilation. Sheath 239 can be made of a metal or a plastic.

When dilation of the tract along guide element 159 is sufficient, dilation element 197 is removed from the body, and high frequency probe 244 is passed over the guide element 159 and into the body towards the target. Sheath 239 can remain in place when dilation element 197 is removed. If sheath 239 remains, its inner lumen 241 is large enough for probe 244 to pass through it. If dilation is not necessary, probe 244 can be passed directly over guide element 159.

Probe 244 has an elongate member or shaft 249. Member 249 can be electrically insulated or thermally insulated by insulation layer 255 over a portion of its length. At the distal portion of member 249, there is an exposed conductive electrode surface 267 from which high frequency current spreads to target tissue and causes heating. Inner channel 271 runs the length of the elongate member 249 and is connected to a surface opening 274 at the distal end of member 249 and proximal opening 277 at the proximal end of member 249. The proximal end has a hub structure 280. Electrical connections (not shown) within member 249 connect the exposed conductive electrode surface 267 to connector 301 at the hub, for connection to an external high frequency generator, as illustrated, for example, in FIG 1D. Referring to FIG. 2, further connections on the hub, such as at connector 307, can connect through the body 249 to temperature sensors, impedance sensors, or other sensors in or near conductive electrode surface 267. Cooling channels, discussed below, can extend within elongate member 249 so that cooled fluid or gas can be circulated through conductive electrode surface 267 and thereby cool conductive electrode surface 267 during the high frequency heating process. Cooling of the conductive electrode surface 267 can result in larger ablation volumes or modified distributions of ablative heating. At the hub 280, fluid input channel 288, when present, can carry cooling fluid to the channels within the probe to the distal portion and tip. Return channels within the elongated member 249 can allow exit of the fluid through exit channel 291. Channels 288 and 291 can connect to an external fluid cooling and circulation system (not shown).

If sheath 239 is left in the tract after dilation element 197 is removed, it acts to further guide probe 244. Sheath 239 can be electrically insulating and can act as the insulation layer for probe 244 in place of insulation layer 255. Hub 280 of probe 244 can connect and lock to hub 240 so that a desired exposed conductive surface such as conductive electrode surface 267 extends beyond tip end 242 of sheath 239. This distance can be pre-determined before probe insertion according to the size of ablation desired.

Inner channel 271 can be constructed from separate segments of metal tubing, or plastic tubing. Inner channel 271 can be an inner lumen in a solid annular tubular structure. Probe 244 can be, for example, a segment of plastic tubing with a lumen 271 and an attached conductive electrode surface 267. Insulation layer 255 can be a thin plastic coating or sheath having a thickness in the range of about 0.001 to 1 mm. A thinner insulation layer can produce less perturbation of the probe 244 surface during insertion and can be suited for coating or insulating rigid metal tubing. For flexible or semi-flexible probes 244, the insulation layer 255 can be the entire wall thickness or a plastic tube covering an inner channel 271, such as a flexible spiral wound or metal tubular number, and in that case, insulation thickness can be larger, for example 1 to 2 mm or greater.

A fluid injection element 320 can fluidly connect to the hub 280 of probe 244. Injection element 320 can be a syringe with plunger 330 for ejecting fluid or gel from its distal tip opening 332. The amount of injected fluid can be quantified by a scale 333. A luer taper 335 mates to a corresponding luer taper 314 of hub 280 of probe 244. If guide element 159 is removed from the high frequency probe 244 after placement of the electrode in the target tissue, fluid agents can be injected through the internal channel 271 and out of the distal hole 274 near the target tissue using fluid injection element 320. For example, hypertonic saline, hypertonic saline gel, toxic or ablative fluids, agents that coordinate with heat ablation to enlarge or modify the ablation volume, anesthetics, or other agents can be injected at the target site through channel 271. Internal channel 271, therefore, can serve both as a guide channel over a guide wire as well as an injection channel for desired fluid or gel agents. Alternatively, a separate injection channel (not shown) within member 249, an injection port at hub 280, and separate injection outflow holes (not shown) in tip 269 can provide a pathway for injection of agents without removing guide element 159.

All or some of the elements shown in FIG. 2 can be used to ablate tissue. For instance, needle 120 can be used with guide element 159 and probe 244. A dilation element 197 can also be used. An injection needle or biopsy device 140 can be used in conjugation with the other elements. An injection device such as injection element 320 can be used. A guide element 159, in the form of a rigid stylet or a flexible guide wire, can be channeled into the body without the use of needle 120. If a guide wire 159 is channeled, for example, into a natural vessel or orifice, such as a blood vessel, urethra, ureter, rectum, colon, intestines, airways or throat, introducing needle 120 can be inserted part way to the target site, and a flexible and steerable, or self-directing and rigid guide wire 159 can be pushed to the target tissue or, in certain circumstances, needle 120 need not be used at all.

The items depicted in FIG. 2 are dimensioned for the particular application of the probe. Smaller diameters are suitable for vascular or delicate organs, or tough tissue, and larger diameters are suitable for less critical regions such as the abdomen, to expand the tissue tract diameter, such as dilation in soft tissue, e.g., skin, fat, abdomen, the limbs, etc., and to guide into organs such as the kidney, liver, lung, etc. Shorter lengths are suitable for shallow targets, e.g., the skin, breast, etc., and longer lengths are more suitable for deeper targets, e.g., liver, brain, etc.

Elongate member 249 of probe 244 can be, for example, a rigid metal tube or a flexible plastic tube. The length of the probe 244 can be in the range of about 10–1,000 mm, depending on clinical needs to reach a target site. The outer diameter of probe 244 can be in the range of about 0.5–10 mm, or greater to suit clinical needs. For example, when a conductive electrode surface 267 has a length in the range of 10 to 40 millimeters and a diameter of 1.0 to 10.0 millimeters and tissue ablation temperatures of up to 90 to 100° C. are achieved in the tissue adjacent to the electrode or at a distance from the electrode, then the ablation diameter can be in the range of about 1 to 10 centimeters, or greater.

One advantage of the system of FIG. 2 is that a tract through the skin and tissue towards the target is established by elements 120, 140, and 159, for example. One or more sequential passes of dilation elements 197 or sheaths 239 of increasing diameter expand the size of the tract in the tissue gently and gradually to achieve the size needed to accommodate the probe 244. This graded tissue dilation can reduce risk of cutting tissue or hemorrhage. Telescoping sets of sheaths 239 or dilation elements 197 can be used and passed over each other to dilate tissue. Probe 244 can then be passed through the tract to the target without the probe 244 perforating or piercing the tissue. The probe merely follows the tract already made by the guidance and dilation elements.

Another advantage of the system of FIG. 2 is that by pre-perforating the tissue and pre-dilating the tract, a large diameter probe 244, for example, having a diameter of 10 mm or more, can be introduced to the target. Such a large diameter probe cannot be pushed directly into delicate tissues or organs with a pointed, cutting tip on the probe, because of the risk of hemorrhage or trauma. However, by gradual tissue dilation and guide element direction of the probe 244, large diameter electrode tips can be placed in target organs easily and safely. Large diameter electrodes can produce large ablation volumes, which can allow larger tumors to be ablated and procedures to be performed in delicate organ environments.

Figure 3:
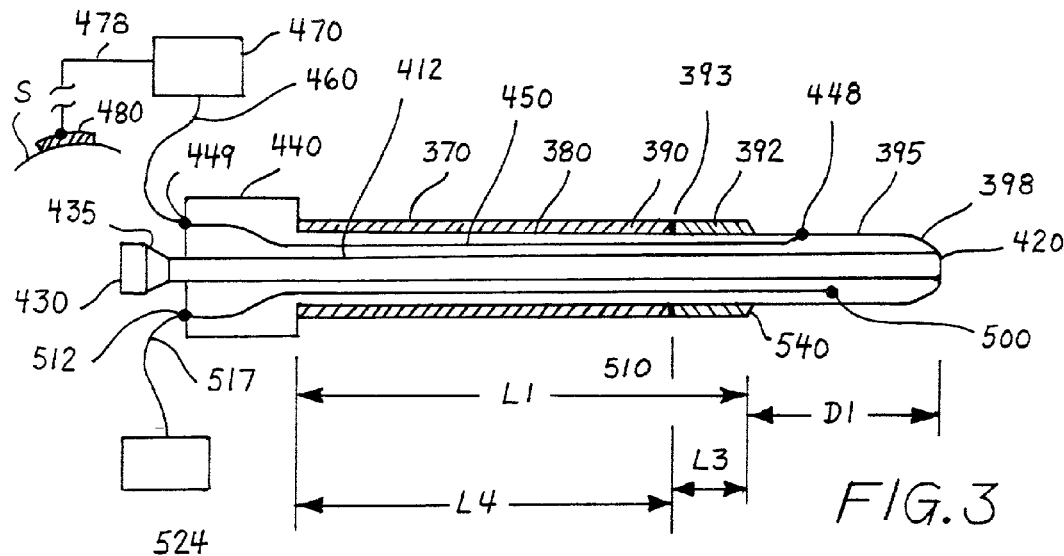
FIG. 3 is a schematic diagram showing an embodiment of a guide element-directed electrode.

Referring to FIG. 3, a high frequency guide wire-directed probe 370 includes an elongate member 380. Member 380 can be formed by a shaft or tube made of metal, plastic, silicone, braided or spiral-wound material, or other construction. Member 380 can be made of MRI-compatible material such as nitinol, titanium, copper, or other metals that do not disturb the MRI images adversely. Member 380 is covered along a length L1 by electrical insulation 390, e.g., a coating such as a fluoropolymer (e.g., polytetrafluoroethylene), polyurethane, polyethylene, or a shrunk-on tubing such as fluoropolymer (e.g., polytetrafluoroethylene), polyethylene, etc., which has sufficient insulating properties to prevent high frequency current from passing through it. The insulation length L1 can be adjusted depending on clinical needs to adjust the exposed electrode length. For example, the insulation can be a slidable sleeve or a shrink-on plastic which can be cut away or altered at the time of surgery by the operator to vary its length. Changing the length of insulation L1 changes a length D1 of an exposed conductive electrode surface 395, which in turn changes the length of ablative heating volume. One or more insulating bands 392 of predetermined length L3 adjoining insulation 390 at joint 393 can be removed at surgery to change the insulation length to L4 and the exposed electrode tip length to D1 plus L3. Alternatively, band 392 can be added to change length L4 to L1. The exposed conductive electrode surface 395 is electrically coupled to member 380, and can be, for example, an extension of metal member 380, or a metal wire, ring, layer or conductive coating on top of a non-metal elongate member 380. For example, exposed conductive electrode surface 395 can be a metal conductive ring that is cemented or secured onto a member 380 that is metal or plastic. If member 380 is made from plastic and is an insulator, then electrical insulation 390 can be eliminated. Member 380 can be rigid, semi-rigid, or flexible. For example, if member 380 is constructed from a metal tube, it can be relatively rigid. If member 380 is, however, constructed from plastic tubing, it can be semi-flexible. When constructed from a spiral metal winding or a braided, woven composite structure of plastic and metal, or plastic alone, or plastic and fibers such as DACRON®, member 380 can be flexible. There can be steering guide wires or pull wires (not shown) within the member 380 that can be used to change its direction or its curvature to suit clinical needs.

Member 380 is shown with a rounded or bullet-shaped distal end 398 and an inner channel 412, which extends from the proximal end near hub 440 to the distal end 398. The inner channel or through opening 412 opens to the external surface of the electrode at the distal opening 420 on the distal end and the proximal opening 430 on the proximal end. Proximal opening 430 includes a luer lock or sealing element 435 so that an injection system can be fluidly sealed to the electrode such that fluids, gels, or other media can be injected through channel 412 and emitted at the distal opening 420. The channel 412 is adapted to pass over a guide element as described above in connection with FIGS. 1 and 2.

Referring to FIG. 3, channel 412 can be formed, for example, by the inner diameter of a metal tube which constitutes an elongated shaft, or by a separate metal tube which is fused to an outer tube represented by member 380 near the tip of the distal end 398 and on the proximal end within the hub 440, leaving an inner space between the inner channel 412 and the insulation 390 for passage of electrical connection wires and other structures. For example, electrical connection wire 450 can connect to exposed conductive electrode surface 395 at connection 448 on the distal end and connects to connector 449 on the proximal end at hub 440. Connector 449 can be connected by a cable 460 to high frequency generator 470 external to the patient's body. Generator 470 can have other connections, such as cable 478, to a reference electrode 480 that is attached to the patient's skin S. In addition, a temperature sensor 500 located within or on the surface of exposed conductive electrode surface 395 can connect via electrical connections 510 to a connector 512 at the hub 440. Connector 512 can be connected further by cable 517 to a temperature-sensing unit 524, which can be part of the external generator 470, for monitoring the temperature at exposed conductive electrode surface 395.

Figure 4:
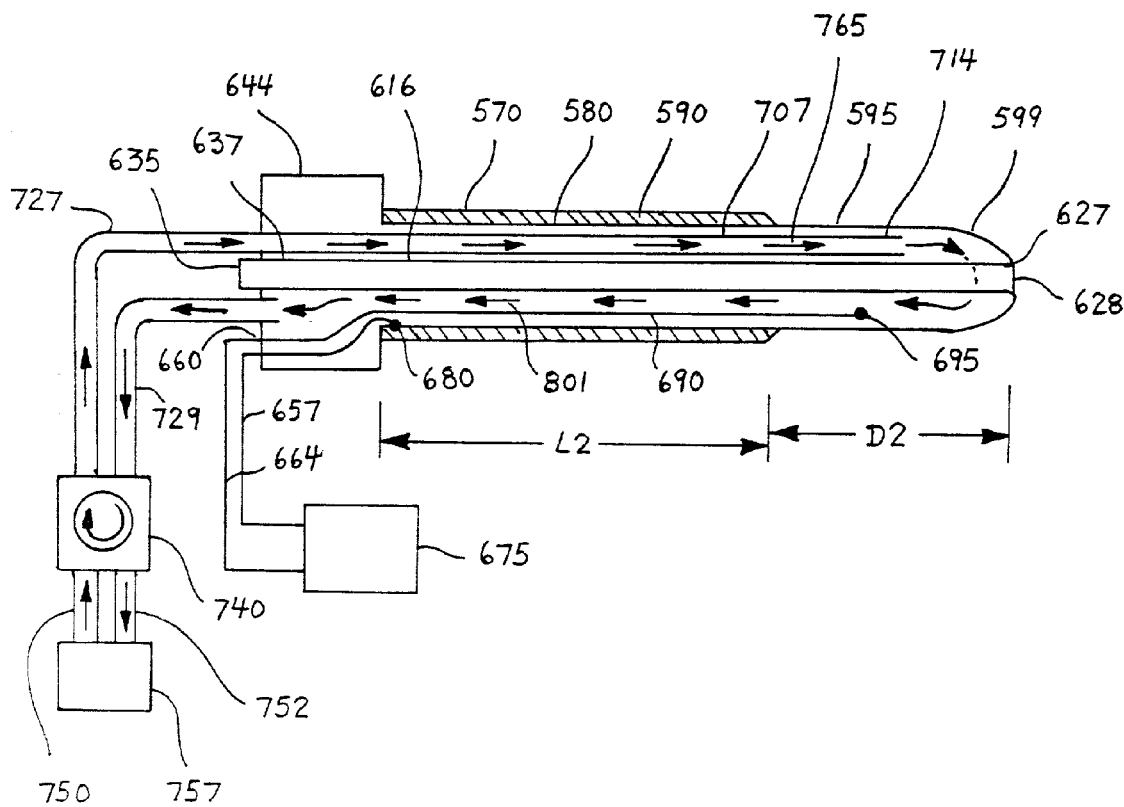
FIG. 4 is a schematic diagram showing an embodiment of a guide element-directed electrode including internal cooling of a conductive tip.

Referring to FIG. 4, another embodiment of a probe 570 is illustrated. Elongate member 580 can be a tubular shaft made of metal or plastic. Member 580 has an exposed conductive tip 595 at its distal portion made of metal as a continuation of member 580 or, alternatively, as a metallized surface or ring attached to a substrate. For example, the electrode tip 595 can be a metallized ring or wire braid, or wire spiral bonded to a plastic substrate such as member 580. A chamber (not shown) can exist within the ring such that fluid can recirculate as indicated by arrows 765 and 801 beneath the ring to cool it. Member 580 has a distal tip 599 that is bullet-shaped, rounded, or septum-shaped, depending on clinical needs. A portion of member 580 can be insulated by insulation 590. The insulation 590 has a length L2 and the exposed conductive member 595 has a length D2. L2 and D2 can be varied by altering the insulation length L2, as described in connection with FIG. 3. Referring to FIG. 4, a through channel or inner chamber 616 runs from the proximal hub 644 to the distal end where it is sealed to the distal tip 599 along a margin 627 to produce a distal opening 628. The seal along margin 627 can be made by welding, swaging, gluing, soldering, solvent bonding, or other joining technique suitable for the metal or plastic nature of member 580 and chamber 616. The seal can be leak resistant to fluids or gases. Similarly, on the hub end a proximal opening 635 connects to the inner chamber 616. The inner chamber 616 is fluid-sealed to the hub at region 637. Thus, there is an inner space between the member 580 and inner chamber 616. Electrical connections to the tip 595 are made via internal wires within that inner space (not shown) or by a connection 680 of connection wire 657 to a metal member 580 which provides electrical connection to generator 675 external to the patient. Electrical connections to temperature sensor(s) 695 (one is shown) in the distal portion of tip 595 are connected by internal connection 690 to an external connection 660, that is connected in turn to the external high frequency generator 675 by cable 664.

Also shown in FIG. 4 are internal cooling channels to cool the exposed conductive tip 595. Channel 707 is within the space between member 580 and inner channel 616. Channel 707 can carry cooled fluid, which can be a liquid or a gas, indicated by arrows 765, to distal end 714 of channel 707 so the cooled fluid circulates inside tip 595. The return fluid flows in another internal channel, as represented by arrows 801. At hub 644, the input channel 707 communicates with external channel 727, and internal channel corresponding to the outward flow 801 communicates with an outward connection 729. Connections 727 and 729 can contain fluid pumped by pump 740 from an external source 757, which connects to the pump 740 by conduits 750 and 752. External source 757 can be, for example, a reservoir of cooled water, saline, or other liquid. For example, a tank of saline can be cooled using ice cubes or a refrigeration system to serve as reservoir 757. The pump 740 can be, for example, a peristaltic pump which captures tubes 750 and 752 to produce a push-pull pumping of fluid to the electrode. Cooling the electrode tip 595 by internal fluid can have the effect of reducing the tissue temperature immediately outside the tip to a low level, for example, in some cases close to 0° C. Then the temperature immediately outside the tip is lower than the tissue, more RF power from generator 675 can be delivered through the tip 595 into the surrounding target tissue before any of the tissue in the ablation region reaches the physically important temperature of 100° C. where steam forms. By cooling the tip, the region of highest temperature in the tissue can be advantageously moved further away from the tip 595 and the volume subscribed by the ablation isotherm of 50° C. can be substantially enlarged relative to ablation isotherms of non-cooled electrode.

A further feature of the guide channel electrode design is that the internal channel, such as channel 616 in FIG. 4, which serves to guide the accurate placement of the probe by a guide element to the target tissue, can also advantageously serve as an injection port for delivery of ablation-enlarging substances at the target site. Injection of an ionic substance such as isotonic saline, hypertonic saline, or saline gel to the target tissue can create an effectively larger, highly conductive region around electrode tip 595. This can reduce the high frequency energy dissipation by frictional heating near the electrode, and can deliver the energy further out into the tissue outside of the plume formed by the injected ionic medium. In this way, an effectively larger ionic electrode can be formed and, accordingly, a larger ablation volume can be made.

The member 580 can be a metal tube with a curved, bullet-shaped distal tip 599. The inner chamber 616 can also be a metal tube that is sealed, soldered, welded, or otherwise connected to distal tip 599 on a margin 627 of the distal opening 628. The inner channels 707 and the exit channel corresponding to arrows 801 can be other tubes within the space between outer tube 580 and inner channel 616. At hub 644, the various channels can be fluid sealed by, for example, potting the hub 644 with epoxy, and the fluid channels can be appropriately connected to external channels 727 and 729 to prevent fluid leaking. The external, internal, and fluid channels can be made from metal or plastic and have other features of CT, MRI, X-ray, or ultrasound compatibility. In one embodiment, the outer tube can be made from plastic, such as polyurethane or polyethylene. Within the channels 707 conduits that carry the fluid toward the tip, along the direction of arrow 765, and outward, along the direction of arrow 801, can be formed.

The member 580 and the inner chamber 616 can have various dimensions, as for example the ranges described in connection with FIG. 2. In one embodiment, for example, inner chamber 616 can have an inner diameter of between 0 and 1 millimeter. The member 580 can have a diameter in the range of: 1.0 to 3 millimeters, 3 millimeters to 5 millimeters, 5 millimeters to 7 millimeters, 7 millimeters to 9 millimeters, or greater than 9 millimeters, depending on the clinical application. Member 580 having larger diameters will allow larger ablation volumes to be achieved. Member 580 having a smaller diameter, such as between 1 and 2 millimeters, can be suited for ablation of tumors having diameters in the range of 10 to 30 millimeters diameter, whereas member 580 having a larger diameter, such as between 2 and 10 millimeters, can be suited for ablation of tumors having diameters in the range of 30 to 100 millimeters, or greater.

The tip shape 599 can be smooth and non-cutting, non-perforating, or non-piercing. One advantage of the probe is that the electrode tip need not be self-tissue piercing, perforating, or penetrating, and it need not have a sharpened point, trocar, or conical point. Rather, the probe can rely on the piercing or perforating characteristics of the guide element such as a sharpened stylet to perforate, puncture, and penetrate the tissue ahead of it. The electrode can, for example, merely dilate the tissue once the tissue has been perforated by the guide element. Alternatively, the electrode may simply pass through the tissue that has already been dilated by a dilation element that has passed over the guide element.

Referring to FIG. 4, the elongated member 580 can have a length in centimeters in the following range: 0 to 1.0; 1.0 to 2.0; 2.0 to 3.0; 3.0 to 4.0; 4.0 to 5.0; 5.0 to 10.0; 10.0 to 20.0; 20.0 to 30.0; or greater than 30.0, depending on the application and depth of tissue tract or target position. Radio frequency output from high frequency generator 765, for example, can be in a range of several hundred kilohertz to 1 megahertz, 1 megahertz to several tens of megahertz, or 100 megahertz or higher. For a cooled electrode, by circulating chilled saline from reservoir 757 such that tip 595 is kept in the range of 0 to 10° C., larger ablative volumes can be achieved than for a non-cooled electrode. With a length of exposed tip D2 in the range of 0 to 3 centimeters and diameter of cooled tip 595 in the range of 1 to 4 millimeters, 100 or more watts of power can be deposited in normal bodily tissue such as the kidney, liver, lung, soft tissue of the organs, or deposited in tumors in those organs, to produce ablative volumes with nominal diameters of several centimeters. For example, application of 150 to 200 watts of power applied to an electrode placed in a kidney tumor, with the duration of the radio frequency being applied for several minutes, for example, in the range of 5 to 15 minutes, can generate an ablation volume having a diameter of 3 centimeters to 6 centimeters, or more. By variation of ablation parameters, for example, size and geometry of electrode, high frequency power deposition, coolant flow or non-flow, the temperature of the coolant, and the time duration of application of high frequency energy to the tissue, variations in the size of ablation volume can be produced and controlled.

Figure 5A:
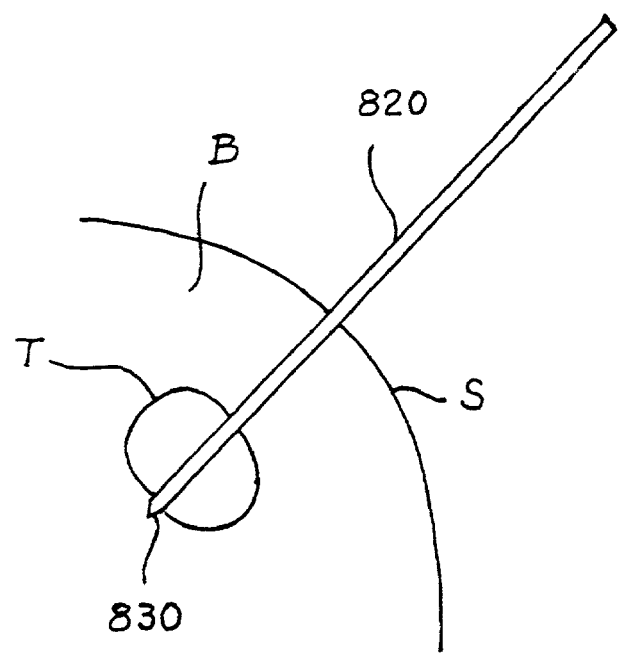
FIG. 5A is a schematic diagram showing introduction of a stylet into a target tissue.
Figure 5B:
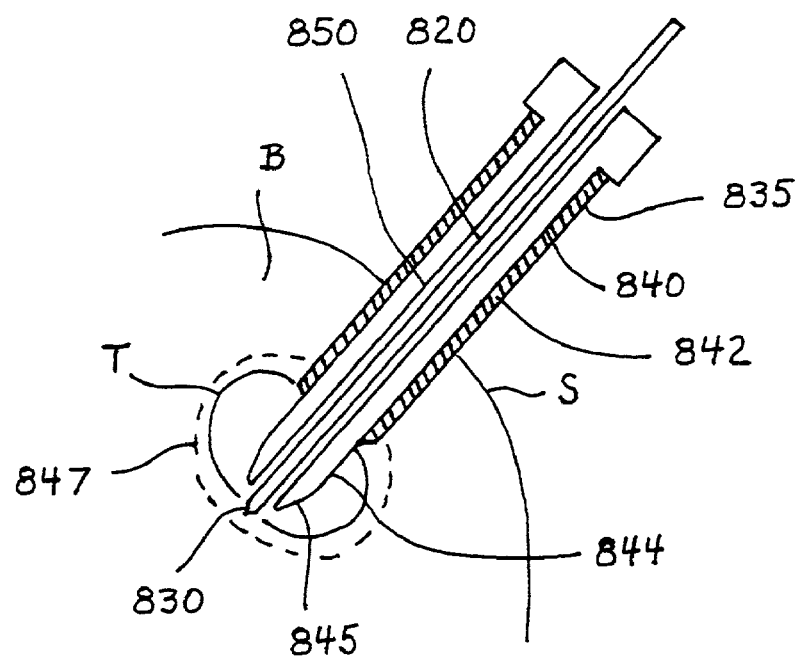
FIG. 5B is a schematic diagram showing a guide element-directed electrode passed over a guide stylet towards the target tissue.

Referring to FIGS. 5A and 5B, a rigid stylet or shaft 820 is directed to perforate and penetrate the skin S, bodily tissue B, and pierce into the target region T. Shaft 820 has a sharpened tip 830 that can pierce, puncture, perforate, and penetrate such tough tissues, including the cortex of organs such as the kidney, liver, lung, and bone. The target tissue T can be a cancerous tumor or other diseased or dysfunctional tissue within the body. Image scanning machines (not shown) can confirm the position and aid in guidance of the shaft 820 towards the target tissue T. Referring to FIG. 5B, electrode 835 is passed over shaft 820 using the tract established by shaft 820. Elongate member 840 has an internal channel 850, which slides over stylet 820. Member 840 has an insulating portion 842 that covers a portion of the shaft 840. The exposed conductive tip 844 has a distal end 845 that is contoured for dilating but not perforating tissue. As electrode 835 is pushed over stylet 820, the tissue can be dilated ahead of it until the tip 844 is at the appropriate position in the target tissue T. At that point, connections to an RF generator (not shown) can be made, as described in connection with FIGS. 1, 3, and 4 above. When the tip 844 is energized with sufficient RF power from an RF generator, an ablation zone indicated by dashed line 847 can be made to engulf all or part of target tissue T. Referring to FIGS. 5A and 5B, shaft 820 is a stiff guiding element that can be inserted into body B without utilizing an initial needle puncture to provide a guide tract to the target. The electrode does not have a self tissue piercing, or cutting, or pointed shape to puncture the skin S or bodily tissues and tissue interfaces.

Figure 6A:
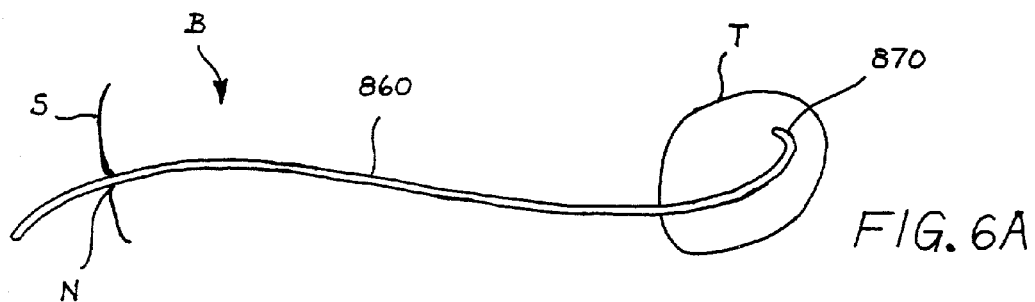
FIG. 6A is a schematic diagram showing a flexible stylet that is introduced into a body and placed near a target tissue.
Figure 6B:
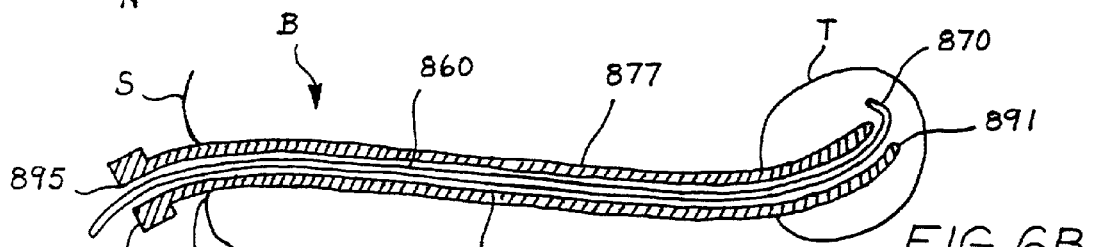
FIG. 6B is a schematic diagram showing a flexible dilation catheter introduced over a flexible stylet and advanced to a target tissue.
Figure 6C:
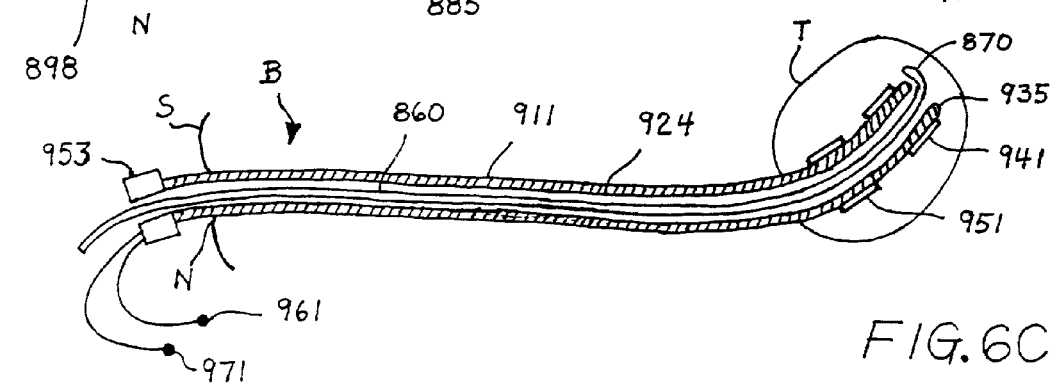
FIG. 6C is a schematic diagram showing a guide element-directed high frequency electrode that is passed over a flexible guide wire to a target tissue.

Referring to FIGS. 6A, 6B, and 6C, a flexible guide element or stylet 860 can be passed through the skin S through a natural opening (not shown) or through a puncture hole N in body B. Guide element 860 can advance through a tract that, for example, is guided by a vessel, or an organ, or an interface between organ or tissue regions. Alternatively, guide element 860 can be advanced through a tract determined by an endoscope, cystoscope, needle, or other entry portal that has been made through the tissue (not shown). Stylet 860 includes distal tip 870, which can be straight or curved. A curved tip or steerable tip 870 (as shown) can facilitate anchoring to target tissue T or facilitate steering the passage of guide element 860 through the tissues in a desired direction, as for example, passing into vessels, ducts, body channels, or spaces between organs.

Referring to FIG. 6B, a dilation element 877 is passed over guide element 860 until its distal tip 891 is appropriately positioned within target tissue T. The dilation element 877 can be flexible and can have a through opening 885 which slips over guide element 860. Dilation element 877 can enlarge or dilate the passageway through the body B and skin S to accommodate further enlarging dilation elements later in the surgical process or to accommodate the high frequency electrode itself. Examples of dilation elements 877 can be flexible plastic sheaths, catheters, or other dilating structures. The dilation element can be relatively flexible, or can have different flexibility along its length to accommodate different tissue sites.

Referring to FIG. 6C, after the dilation is sufficient, as illustrated in FIGS. 6A and 6B, a flexible high frequency electrode shaft 911 is passed over guide element 860 until distal end 935 of shaft 911 is appropriately positioned in tissue T. Shaft 911 can have one or more electrodes, such as electrodes 941 and 951, which are exposed and conductive at its distal portion. These electrodes are connected to the hub structure 953 via electrical connections (not shown) within elongated electrode shaft 911, which in turn is connected to external apparatus (not shown) via connectors 961 and 971, respectively, that provide high frequency signals or thermal sensing apparatus, etc., as shown in connection with FIGS. 1, 3, and 4 above. Referring to FIG. 6C, the elongated electrode shaft 911 can be a plastic sheath, catheter, or tubing having a through opening 924 from hub end 953 to distal end 935. The electrode shaft 911 can be flexible and have electrical connections, fluid cooling channels, monitoring connections, etc., embedded in its walls to communicate from its proximal hub end 953 to its distal portion where a tip 935 and electrodes 941 and 951 are located. A probe having flexible guide element 860 and electrode shaft 911 can be advanced into vessels or natural openings within the body. For certain organs such as in the colorectal area, throat, lungs, peritoneum, or vessels anywhere in the body, such an electrode system is well suited. The electrode can go around curves and corners, it need not be rigid, nor does it have a tissue-piercing quality. The curved tip 870 on the guide element can anchor and stabilize distal portion of electrode shaft 911 in the target tissue, which is advantageous when the target is in organs such as the lung, kidney, liver, peritoneum, and other sites where movement due to respiration, manipulation, or soft tissue flexibility can be a problem in maintaining the position of electrode shaft 911 at its proper site for heat ablation and imaging.

Figure 7:
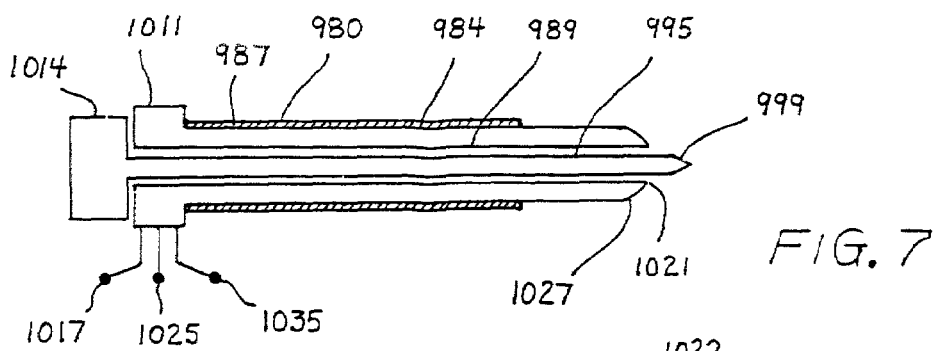
FIG. 7 is a schematic diagram showing an embodiment of a guide element-directed electrode with a straight, pointed stylet as a guide element.

Referring to FIG. 7, an electrode 980 has elongated element 984, which can be rigid or non-rigid, and insulated portion 987. Electrode 980 has a substantially concentric inner channel 989, and hub 1011. Inside electrode 980 is a rigid straight stylet system 995 which has sharpened point 999 that protrudes from the distal opening 1021 of rounded distal end 1027 of member 984. The stylet has hub 1014, which can match to hub 1011 of the electrode such that the entire assembly of electrode and stylet can be pushed through the tissue in unison. Stylet 995 can be electrically insulated or conductive. The high frequency electrode 980 advantageously does not have a pointed, sharpened, tissue piercing, perforating, or puncturing distal end. Rather, the stylet 995 has a sharpened point 999 which serves to puncture, pierce, perforate, and penetrate the tissue. The electrode 980, in its position outside stylet 955, thus follows along the tract which has been made by the penetrating point 999. Electrical, thermal, water-cooling connections such as 1017, 1025, and 1035 can be made for the electrode through its hub end 1011, as described previously in connection with FIGS. 3 and 4.

Figure 8:
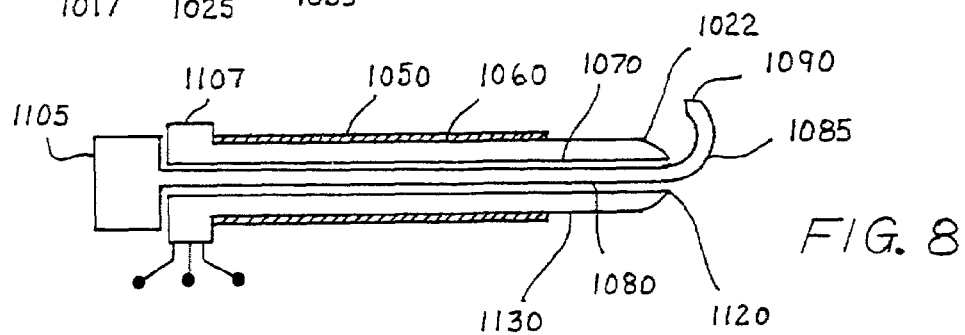
FIG. 8 is a schematic diagram showing an embodiment of a guide element-directed electrode placed over a curved tip anchoring guide element.

Referring to FIG. 8, an electrode 1050 includes shaft element 1060, inner channel 1070 and hub 1107. A stylet 1080 has curved tip 1085 and sharpened point 1090. Stylet 1080 includes a hub 1105 that can be moved relative to electrode hub 1107 so as to retract and rotate curved tip 1085. Stylet 1080 can be withdrawn relative to shaft element 1060 such that point 1090 starts to emerge from the opening 1120 at distal portion of inner channel 1070 so as to penetrate tissue during insertion. The electrode tip 1022 follows point 1090 through the tissue without actually puncturing, piercing, or perforating the tissue itself. Once in place, the curved portion 1085 can be extended beyond the distal opening 1120 of the electrode such that it anchors to the target tissue. Multiple curved anchors similar to 1085 can emerge at different azimuthal angles or positions at the tip. After anchoring, the electrode hub 1107 and stylet hub 1105 can be locked together (lock mechanism not shown) such that the exposed conductive tip 1130 is stabilized in position relative to the target tissue.

Figure 9:
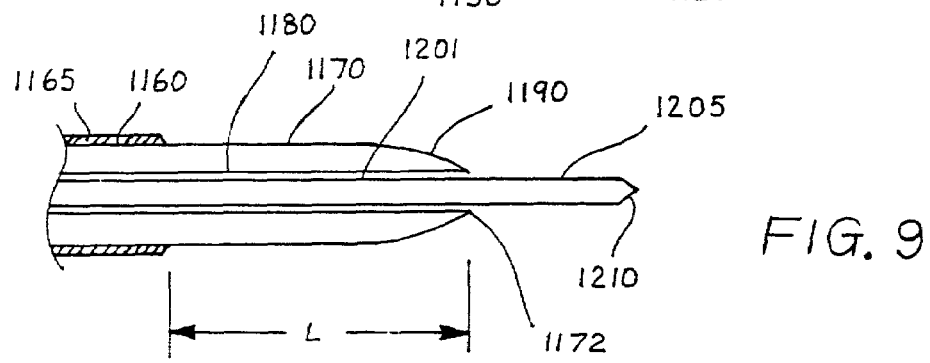
FIG. 9 is a schematic diagram showing a tip of a guide element-directed electrode having a bullet shape together with a pointed guide element.

Referring to FIG. 9, a distal portion of a guided electrode and stylet can include exposed conductive tip 1170 having a length L. Insulation 1165 can cover the rest of an elongated member 1160. Inner channel 1180 meets the outer surface of tip 1170 at distal opening 1172 of a bullet-shaped nose 1190 of elongated member 1160. The bullet-shaped nose 1190 has a convex, smooth taper that is coaxial with the inner channel 1180 and opening 1172. By itself, tip 1170 is non-perforating or non-piercing and it has non-pointed and non-cutting contours and it is not well suited to perforate skin or tissue because a tapered tip with a hole in it is not desirable to perforate skin or tissue. A guide element 1201, such as a stylet or guide wire, includes emergent tip 1205 with pointed distal end 1210. The guide element 1201 can be placed in the body by needle insertion or other means such that distal end 1205 is near the target tissue. The electrode 1160 slides over the guide 1201 such that the tip 1170 is in the appropriate place relative to target tissue or volume. The bullet-shaped distal nose 1190 facilitates electrode passage through the tissue because of its graded, smooth, and septum shape. The puncture, perforation, and penetration of the tissue initially have been done by the pointed stylet tip 1210, making it unnecessary for the bullet-shaped distal nose 1190 to have a sharpened or cutting point. The length L of tip 1170 can be changed or graded by adjustment of the position of insulation 1165, as described previously.

Figure 10:
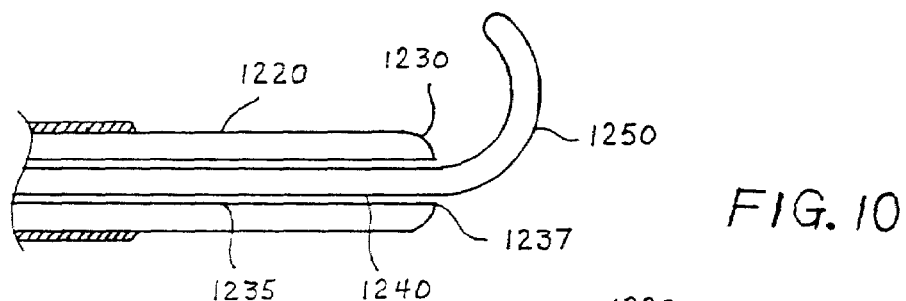
FIG. 10 is a schematic diagram showing a rounded tipped guide element-directed electrode together with a curved guide element.

Referring to FIG. 10, a distal portion of a guided electrode and stylet can include electrode tip 1220 having a blunt and rounded end 1230. Internal channel 1235 meets a radiused end or blunt end 1230 at an opening 1237. A guide element 1240 has a curved tip 1250 (or multiple tips, not shown) for anchoring the element in the target tissue. The guided electrode can have a smooth blunt tip shape which by itself can be unsuitable for puncturing, piercing, perforating, or penetrating tissue. By use of dilation elements over guide wire 1240 before introducing an electrode having a blunt tip shape, or in situations where there are natural channels or orifices in the body to pass through, the blunt electrode tip 1220 can be passed over the guide wire to the target, which can be an advantage where delicate tissue or highly vascular tissue might be encountered. For example, a slender guide wire element 1240 could be put into the spinal spaces, the heart, or the spine itself, or it could be placed in vascular organs such as the kidney or liver. The guide wire can have an outer diameter of 0 to 0.5 millimeters, 0.5 to 1 millimeter, or 1 millimeter to 2 millimeters, and thus be very discrete upon insertion. The guide wire can be insulated or coated so it does not perturb the shape of the ablation volume made by the electrode tip. The electrode 1220 can be subsequently slid over the wire with its tip 1230 gently traversing tissue on the way, reducing the risk of perforating or cutting critical structures or blood vessels. The electrode, in this case, could be rigid or flexible, depending on application.

Figure 11:
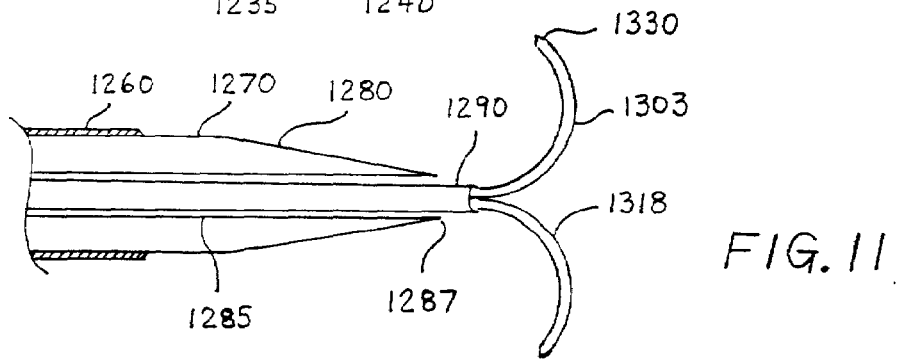
FIG. 11 is a schematic diagram showing a conical-shaped tip of a guide element-directed electrode together with a multi-pronged anchoring insulated guide element.

Referring to FIG. 11, an electrode tip can include electrode shaft 1260 having an exposed tip 1270 which has a conical or septum shaped surface 1280 at its distal end. Conical shaped surface 1280 is axially symmetric and meets an inner channel 1285 of shaft 1260 at the junction 1287 of the distal opening. The surface 1280 can be a straight taper or convex taper. Internal guide element 1290 can have a tubular structure having a metal jacket, or in another version, an insulating jacket such as a plastic tubing or plastic insulation over a metal tube. Inside element 1290, or emerging from it, are multiple curved anchors 1303 and 1318. There can be one or a multiplicity of such anchors. The anchors can have pointed tips such as tip 1330 to pierce tissue along their curved arc. Element 1290 can include a bundle of two, three, four, five, or more separate wire elements with curved tips like anchors 1303 or 1318 that emerge from junction 1287 to form an umbrella of tissue anchors. Each anchor can be insulated. The curved anchors like 1303 and 1318 can be made of precurved wire or tubing, such as Nitinol. The curved anchors can be pushed out of guide element 1290 by an actuator on the proximal end of the element 1290 (not shown). The advantage of such an embodiment is that the septum or conical shaped surface 1280 of the exposed tip 1270 can separate tissue and push it laterally with a mechanical advantage that could be useful when penetrating cartilage, muscular or cortex layers. The surface 1280 meets the lumen or inner channel 1285 at junction 1287 which by itself is not perforating or not piercing to skin or tissue since. The junction 1287 is not pointed and tissue will pack up into lumen 1285, making it undesirable to push shaft 1270 directly into skin and tissue without a stylet or guide element in lumen 1285. If the electrode shaft 1260 is rigid or semi-rigid, pushing longitudinally on the electrode can produce a mechanical leverage and high lateral force against surface 1280 so as to dilate and push the tissue apart and away from the path made by guide element 1290. If the inner diameter of channel 1285 is, for example, a fraction of a millimeter larger than outer diameter of guide element 1290, then the advancement of the electrode shaft 1260 over the guide wire in bodily tissue will not result in aggregation or packing of the tissue into the space between the channel 1285 and the guide element 1290. An advantage of a configuration shown in FIG. 11 is that if the electrode body is rigid or semi-rigid, it can go over the guide element and penetrate tissue while not piercing or perforating tissue initially or along the tract to the target tissue.

One of the advantages of a guide wire directed electrode is that the through opening in the electrode and the hole in the tip can enable passage of injectable agents such as hypertonic saline and gel, as described above. The through opening also allows the passage of markers, or marker dyes, that can be placed at the target tissue region following heat ablation. These markers can be visualized by imaging devices such as CT, MR, X-ray, or ultrasound for confirmation of position or re-targeting at a later time. The markers can be, for example, gold seeds, tantalum seeds, or radiopaque, MRI, or ultrasound visible fluids, gels, or media that can be detected and imaged. Advantageously, the guide wire and electrode system can be separate elements. The guide wire system and its penetration device such as a needle can provide the perforating and puncturing of the skin and tissue. The guide wire system and its penetration device can also be highly compatible to image guidance. For example, they can be MRI compatible so as to leave minimal artifact in an MRI scan, they can be CT compatible with minimal X-ray scattering to reduce artifact in CT or X-ray images, or they can be ultrasound ecogenic, and thus visible in ultrasound scanning. As a consequence, placement and targeting can be simplified for the surgeon using the guide wire and its introducer. Later, when the electrode is passed over the guide wire, the electrode placement need not be image guided. For example, the electrode can be made of a non-MRI-compatible material. Since the MRI was used during the guide wire introduction and placement phase, it may not be necessary to do further MRI scans when the electrode is in place. The same is true for CT, X-ray, and ultrasonic scanning, in each case the guide wire can be highly compatible with imaging. This can mean that the high frequency ablation process with the electrode in place can be done offline from the image scanning suite, which can save considerable time in the image scanning suite, and save considerable expense, time, manpower, and technician fees.

Figure 12:
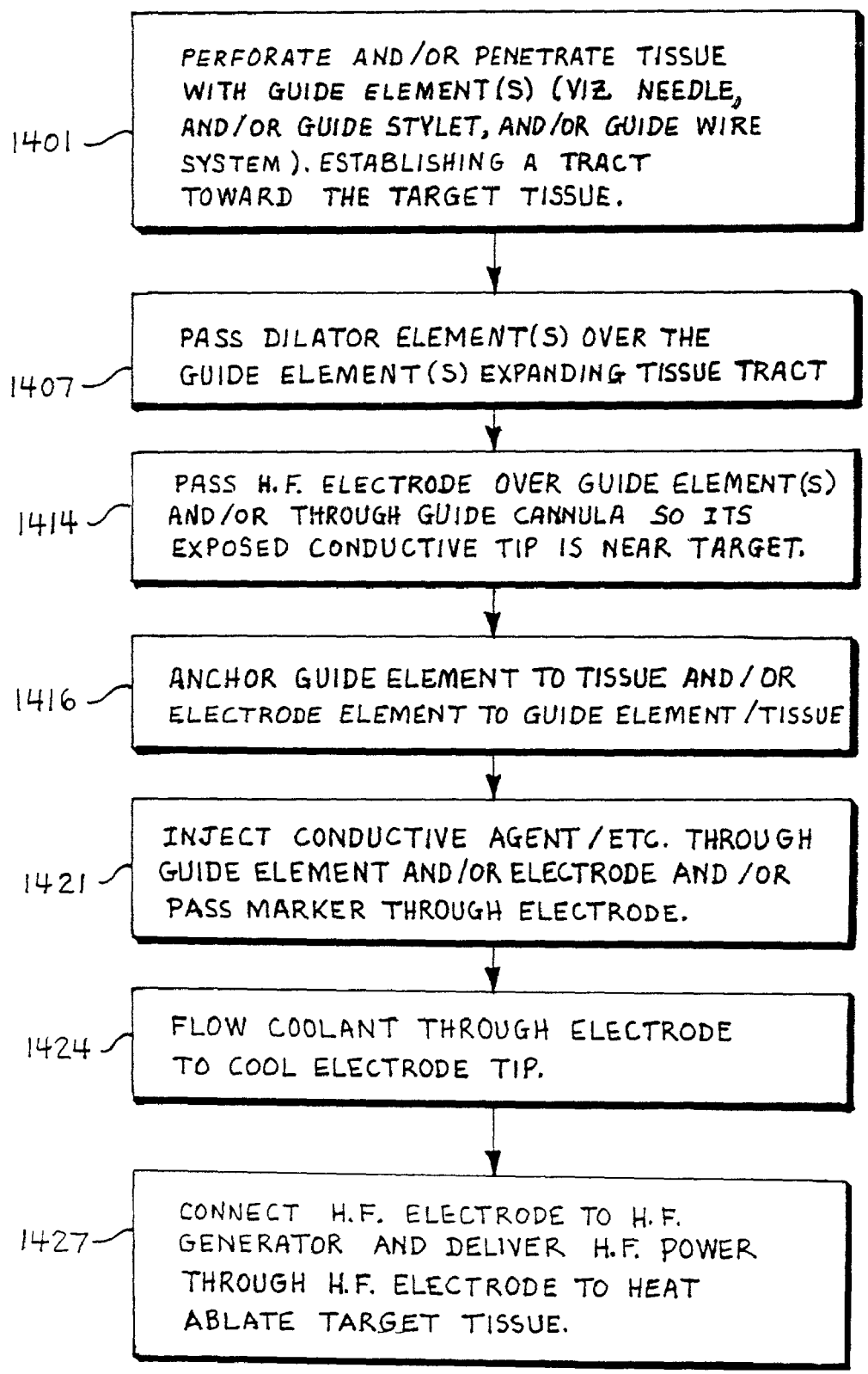
FIG. 12 is a flow chart showing a process for employing a system including a guide element-directed electrode.

Referring to FIG. 12, the procedure starts by perforating and/or penetrating tissue with a guide element or multiple guide elements (step 1401). For example, a needle with stylet can be used initially, followed by a guide stylet or guide wire, as described above. The guide elements establish a tract towards the target tissue. This can be done under image guidance control such as CT, MR, X-ray, or ultrasound.

The next step is to dilate the tract to the target by passing one or more dilation elements over the guide element to expand the diameter of the tract (step 1407). The dilation elements can be removed after expanding the diameter of the tract. Alternatively, the dilation elements can remain in place if the electrode is configured to pass over them. For example, a guide cannula can be over the dilation element and removed or left in the tract when the guide element is removed.

The next step is passing a high frequency electrode with its internal guide channel over the guide element or elements, or alternatively over the dilation elements, so that the exposed conductive tip of the electrode is at the appropriate position near the target tissue (step 1414).

The next step is to anchor the guide element to the target tissue or other tissue, or to anchor the electrode element to the guide element and/or bodily tissue (step 1416). This serves to immobilize the conductive tip to the desired position relative to the target tissue, reducing its movement to the respiration, manipulation, and other bodily movements.

The next step (1421), which can be optional, is the injection of conductive agents or other agents through either the guide element orifices or, if the guide element is removed or appropriately configured relative to the electrode, through the through opening of the electrode so that it passes out the hole in the tip of the electrode into the region of the target tissue. Saline, hypertonic saline solution, hypertonic saline gel, alcohol, chemotherapeutic agents, or RF ablation enhancing elements can be introduced in this manner. A marker element(s) or substance can be passed through the electrode through opening and left in or anchored to the tissue for future image guidance reference, for example, when following the progress of the ablation and tissue or tumor site.

The next step (1424), which is also optional, is to connect a cooling fluid source to the electrode, and begin flowing cooling fluid or gas through the electrode so as to cool the electrode tip.

The next step (1427) is to connect the high frequency electrode to a high frequency generator located outside the patient's body. The output of the generator can be increased, causing heating of the target tissue near the exposed electrode tip. The high frequency generator can be configured to monitor parameters such as electrode temperature, cooling fluid temperature, RF power, current, voltage, impedance, and time of power application. The generator system can be controlled in coordination with and including a cooling reservoir and fluid pumping system in the case that coolant channels are provided within the electrode to cool the electrode tip during ablation.

All or only some of these steps may be used in accordance with the invention. For example, each of step 1407, step 1416, step 1421, or step 1424, independently, can be eliminated to suit clinical needs.

Figure 13:
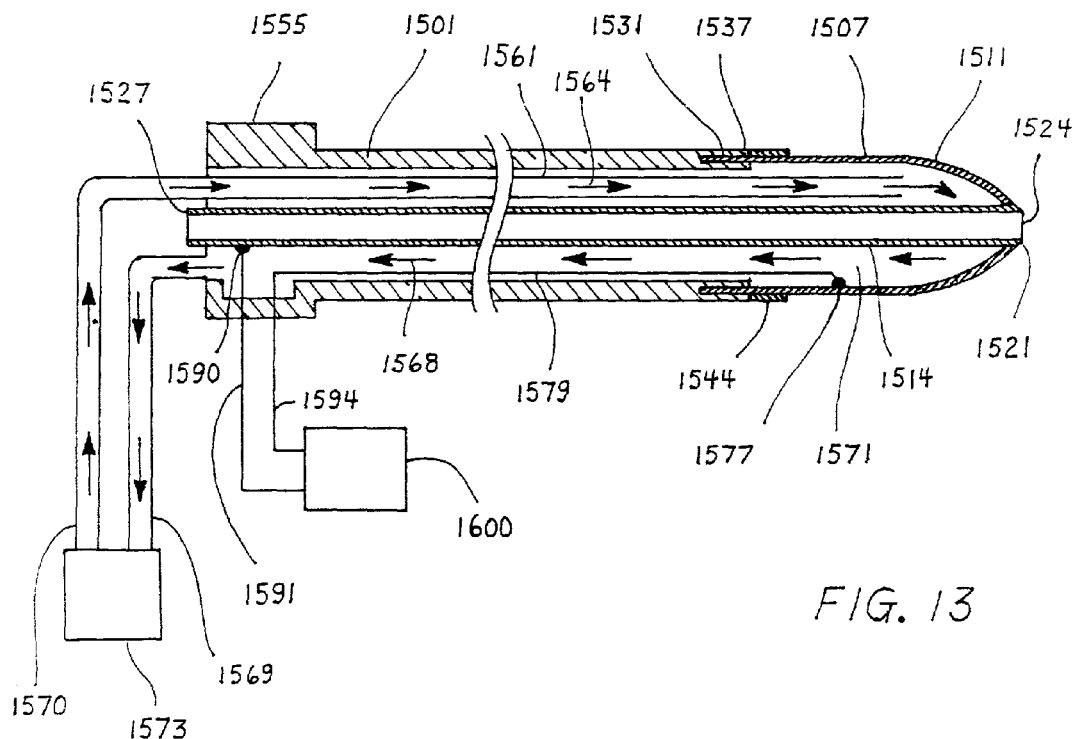
FIG. 13 is a schematic diagram showing a flexible shaft guide element-directed electrode having a metal distal tip with internal cooling channel.

Referring to FIG. 13, a guide element-directed electrode, shown in sectional view, includes an elongated outer portion 1501 and an electrode tip 1507. The elongated outer portion 1501 is made of a material to enable lateral flexing of the electrode shaft, such as a plastic. The portion 1501 is a tube that can be made of a silicone, a fluoropolymer (e.g., polytetrafluoroethylene), a polyurethane, a polyethylene, or other appropriate material. Elongated outer portion 1501 can be of various diameters to enable various degrees of lateral flexibility and longitudinal stiffness to make it suitable for clinical needs, such as the consistency of the tissue that the electrode penetrates. The electrode tip 1507 is a metal, conductive shell at the distal end of the electrode. Electrode tip 1507 is joined to the flexible elongated outer portion 1501 at junction 1531, which can be a glued or mechanical bond. A lip portion 1537 of the flexible elongated outer portion 1501 can extend over or under the distal end of tip 1507 near junction 1531 to provide added strength and strain relief to the junction. An added insulation segment 1544 on the outside of tip 1507 and extending beyond lip 1537 can be removed to change the exposed length of the conductive surface of tip 1507 and thus to change the size of the ablation volume produced by the electrode. Distal portion 1511 of tip 1507 is tapered down to join a guide tube 1514 along an annular junction 1521. Guide tube 1514 can have a thin wall and can be made from a metal, a plastic, or a plastic-metal composite. Tube 1514 can be glued, fused, soldered, welded, or otherwise joined to tip 1507 at the junction 1521 to form a distal guide tube opening 1524. Guide tube 1514 can have lateral flexibility if it is made of plastic tubing or if it is made of thin-walled metal tubing, for example, having a small diameter such as about 1.5 millimeters or less. Guide tube 1514 can be made of a plastic tube having a braided, helical or other reinforcement that can contribute strength and flexibility, for example, a metal reinforcement. At the proximal end of the elongated outer portion 1501, there is a hub 1555 which contains a proximal opening 1527 to the guide tube 1514. Guide tube 1514 is fluidly sealed to hub 1555.

Elongated outer portion 1501 includes internal channel 1561 which carries cooling fluid that flows distally indicated by arrow 1564 to the chamber 1571 that is inside tip 1507. The cooling fluid cools tip 1507. Channel 1561 can be a metal or a plastic tube or can be molded into outer portion 1501. Return flow of coolant in another internal channel towards the proximal end of the electrode is indicated by arrow 1568. External tubes 1570 and 1569 carry the coolant between the probe and the coolant source 1573.

High frequency generator 1600 connects to the electrically exposed portion of tip 1507 by connection wires 1591 or 1594. Internal guide tube 1514 can be a metal tube, and high frequency connection wire 1591 can connect to guide tube 1514 at junction 1590. Temperature sensor 1577 is in contact with or in proximity to tip 1507 to measure the temperature of the tip 1507 or of the coolant that flows through tip 1507. Internal connector 1579 and external connection wire 1594 connect sensor 1577 and generator 1600, which can read out and display the temperature detected by sensor 1577.

Figure 14:
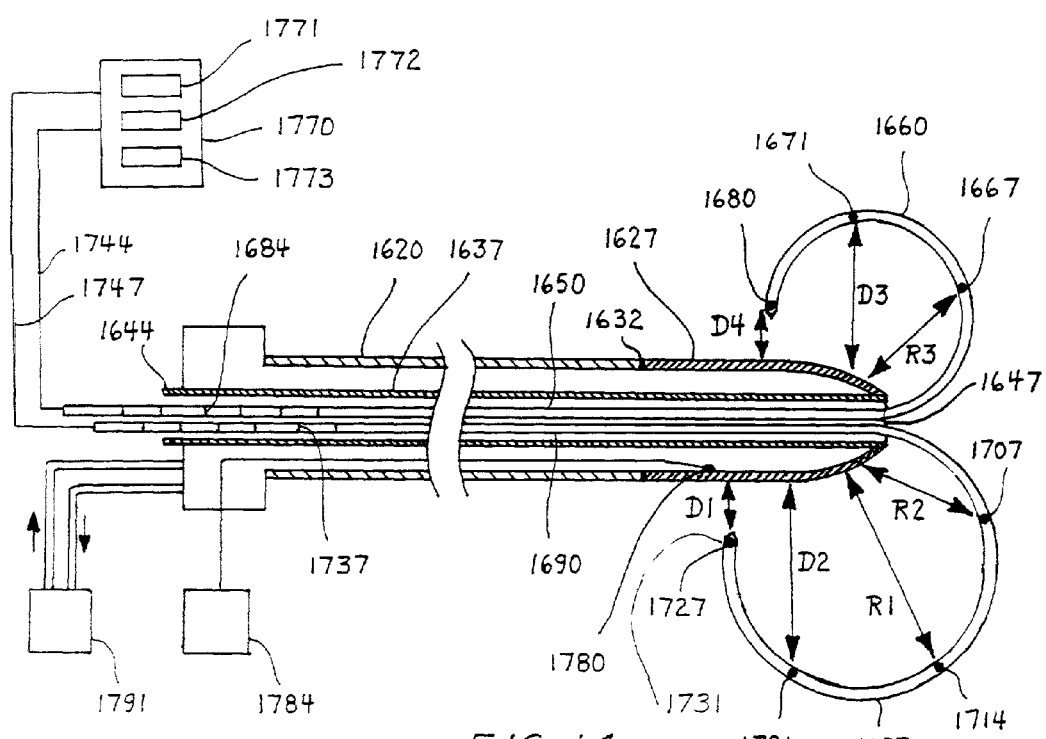
FIG. 14 is a schematic diagram showing a guide element-directed electrode with a flexible plastic outer shaft joined to a metal distal tip and temperature monitoring curved anchoring elements extending from an internal guide element.

Referring to FIG. 14, a guide element-directed electrode includes an elongated flexible portion 1620 is connected to an exposed conductive tip 1627 at junction 1632. Portion 1620 can be made from a plastic. Tip 1627 can be made from a metal. An internal guide channel 1637 has an opening 1644 at its proximal end and opening 1647 at its distal end. Channel 1637 can be made from metal or plastic tubing. The internal lumen of 1637 can pass over a guide element already in the patient's body. An external generator 1784 supplies energy to tip 1627 by connection 1780. A coolant supply 1791 provides coolant to tip 1627.

The guide element inside of channel 1637 includes element 1650, which can be a wire or tubing that extends through distal opening 1647 and has an off-axis distal portion 1660. Portion 1660 follows an off-axis path such as a curved arc and has different degrees of extension from port 1647 depending on the degree of penetration of element 1650 into channel 1637. The degree of penetration is indicated by the depth markers 1684 on element 1650, which can be viewed relative to opening 1644. As the degree of penetration increases, the tip 1680 of portion 1660 can pass the location 1667 at an angle and distance from tip 1627 indicated by arrow R3. At further penetration of element 1650, tip 1680 can pass point 1671 at lateral distance D3 from tip 1627. At still further penetration, tip 1680 can move to distance D4 away from tip 1627. Tip 1680 can carry a temperature sensor, impedance sensor, or other physical sensor to measure the corresponding physical valve of the tissue near tip 1627 during the ablation process. Information from the sensor at tip 1680 is carried by connection 1744 to apparatus 1770 which displays the temperature, impedance, or other physical parameters on readout 1771.

Another component of the guide element inside of channel 1637 is guide wire 1690 that also extends from distal opening 1647. The curved portion 1697 of wire 1690 follows an arcing path with positions: 1707 at vector R2, 1714 at vector R1, 1721 at distance D2, and 1727 at distance D1 from tip 1627. As element 1690 is pushed into channel 1637, the tip 1731 will pass from the hole 1647 along the path of the arc 1697. Tip 1731 will reach all the positions of points along that path, including, for example, the vector positions R2, R1, D2, and D1, according to the depth of position of element 1690 inside channel 1637. The depth of position can be measured by marks 1737 on element 1690 as they pass near opening 1644. A temperature sensor in tip 1731 can detect tissue temperature as the tip 1731 passes positions such as R2, R1, D2, and D1. Connection 1747 from element 1690 to apparatus 1770 enables readout 1772 to register the temperature of the tissue near tip 1731. Element 1690 enables a mapping of temperature in space around tip 1627 during heat ablation of tissue in proximity to tip 1627. Since tip 1627 explores a different path than tip 1680 of portion 1660, more detailed information on ablation temperature distribution and the size of ablation volume can be determined. One, two, or more spatial probes such as 1660 and 1697 can be deployed around tip 1627. The spatial probes can emerge either through opening 1647 or through other openings (not shown) along the shaft of elongated flexible portion 1620 or through tip 1627 to accommodate the extent of thermal mapping desired. Portions 1660 and 1697 can be electrically insulated to prevent unwanted perturbations of ablation fields around tip 1627. Alternatively, portions 1660 and 1697 can be uninsulated and can be raised to RF potential along with tip 1627 to enhance ablative heating volume along their paths.

Referring to FIG. 15, a guide element-directed electrode 1800 has a flexible elongated element 1804 which can be made from a plastic. Element 1804 includes a hub 1860. Element 1804 is bonded to conductive ring 1814 at junction 1816. Element 1807 is a continuation of element 1804 and is bonded to ring 1814 on the distal portion at junction 1818. A distal tip 1824 has a tapered or conical shape 1846 and is made from a plastic or metal material. Tip 1824 is bonded to element 1807. Guide tube 1836 inside element 1804 has proximal hub opening 1864 and distal opening 1857, and is joined to tip 1824. The conical shape 1846 of tip 1824 meets opening 1857 at circular edge 1838. Connection 1914 connects the junction 1900 at ring 1814 to external connection 1918 and apparatus 1924. Apparatus 1924 can be a high frequency generator and readout of sensors at junction 1900 such as a temperature sensor, an impedance sensor, or other physical sensors. Coolant supply 1896 pumps coolant into electrode 1800 through conduit 1890. Coolant flows out of conduit 1890 and through internal channels of element 1804 shown by flow arrows 1870 and 1880. The coolant flows through the region 1940 proximate to ring 1814 to cool ring 1814. The coolant return-flows from region 1940 through region 1942 inside ring 1814 to further cool ring 1814. The coolant return-flow is indicated by flow arrows 1881 and 1874 and returns to coolant supply 1896 by conduit 1892.

Referring to FIG. 16A, a cross-sectional view through electrode 1800 of FIG. 15 at the position indicated by the dashed line A, includes e the extension of plastic element 1804, which contacts ring 1814. Guide tube 1836 and has inner lumen 2021 inside it which is the guide channel of the electrode. Webs 2012 and 2014 support guide tube 1836 within element 1804 and divide the space between tube 1836 and element 1804 into two regions 1940 and 1942. Coolant flow in region 1940 corresponding to inflow arrow 1870 in FIG. 15 is designated by crossed circle 2039 in FIG. 16A. Coolant flow in region 1942 corresponding to outflow arrow 1874 in FIG. 15 is designated by dotted circle 2037 in FIG. 16A. Connection 1914 carries high frequency current to ring 1814. Wire 2044 in region 1940 (not shown in FIG. 15) can carry signals related to temperature measurements from a sensor in electrode 1800. Plastic element 1804, tube 1836 and webs 2012 and 2014 can be made of plastic such as polyurethane, polyethylene, silicone, etc., and can be extruded or molded in one piece.

Referring to FIG. 16B, a cross-sectional view through electrode 1800 of FIG. 15 at the position of the dashed line B shows the regions 1940 and 1942, which extend out from the tube 1836 to the ring 1814. Webs 2012 and 2014 extend out to the ring 2004 so that coolant flowing inward or distally in region 1940 in the direction indicated by crossed circle 2039 and outward or proximally in region 1942 indicated by dotted circle 2037. Webs 2012 and 2014 directly contact ring 1814 for direct thermal communication with ring 2004. The wall portion 1804 of FIG. 16A is not present in the section shown in FIG. 16B, Referring to FIG. 16C, a cross-sectional view through electrode 1800 of FIG. 15 at the position of the dashed line C. shows the element 1807. Holes 2064 and 2067 in webs 2012 and 2014 fluidly connect region 1940 and region 1942. Coolant inflow indicated as cross circle 2039 in FIGS. 16A and 16B continues in FIG. 16C as flow direction 2070 through hole 2064 and flow direction 2074 through hole 2067, by which the coolant moves from region 1940 to region 1942. When in region 1942, the coolant continues its proximal flow as indicated by dotted circle 2037 in FIG. 16B. Referring to FIG. 16C, the flow arrows 2070 and 2074 correspond to the transition from flow arrow 1880 to flow arrow 1881 in FIG. 15.

Probes including a flexible elongated shaft connected to a conductive electrode tip as illustrated in FIGS. 13, 14, 15, 16A, 16B, and 16C can have several advantages. The flexible elongated shaft can make it convenient to pass the electrode over a guide element that is curved. For example, the guide element can be a flexible structure that follows the curves of a natural vessel, or the guide element can be a stylet that is deflected and curved in an arc as it penetrates through tissue regions of different texture and shape. As an example, making the flexible elements 1501, 1620, or 1804 as in FIGS. 13, 14, and 15 from a plastic or a rubber material such as polyurethane, polyethylene, polyester, or silicone can provide lateral flexibility to follow curved paths as well as sufficient longitudinal strength to pass over a guide wire to penetrate and follow a tissue tract.

Electrode shapes 1511, 1627, and 1846 as in FIGS. 13, 14, and 15 can be convergent shapes such as straight conical sections, as for example shape 1846, or tapered dilating shapes, as for example shape 1511, to more easily penetrate tissue or dilate tissue along a tract established by a guide element over which the electrode is passed. A non-blunt distal tip such as conical shape 1846 or convergent dilation shape 1511 can be made either from a metal as part of the exposed conductive electrode or from a plastic if it is desired to have tip end not be part of the ablation-producing portion of the electrode. For example, in FIG. 13, tip 1507 can be a continuous metal shell made by machining the shape or by drawing or pressing the shape. When connected to high frequency voltage, the entire exposed tip 1507, including its distal-most portion 1511, is active in delivering the heat ablating current to the surrounding tissue. In another example, in FIG. 15, conical tip 1824 at the extreme distal end of the electrode can be made of a solid or a hollow plastic material 1846 that is electrically insulating. In that case, only the exposed portion of metal ring 1814 is active in delivering the heat-ablating current to the tissue.

Figure 17:
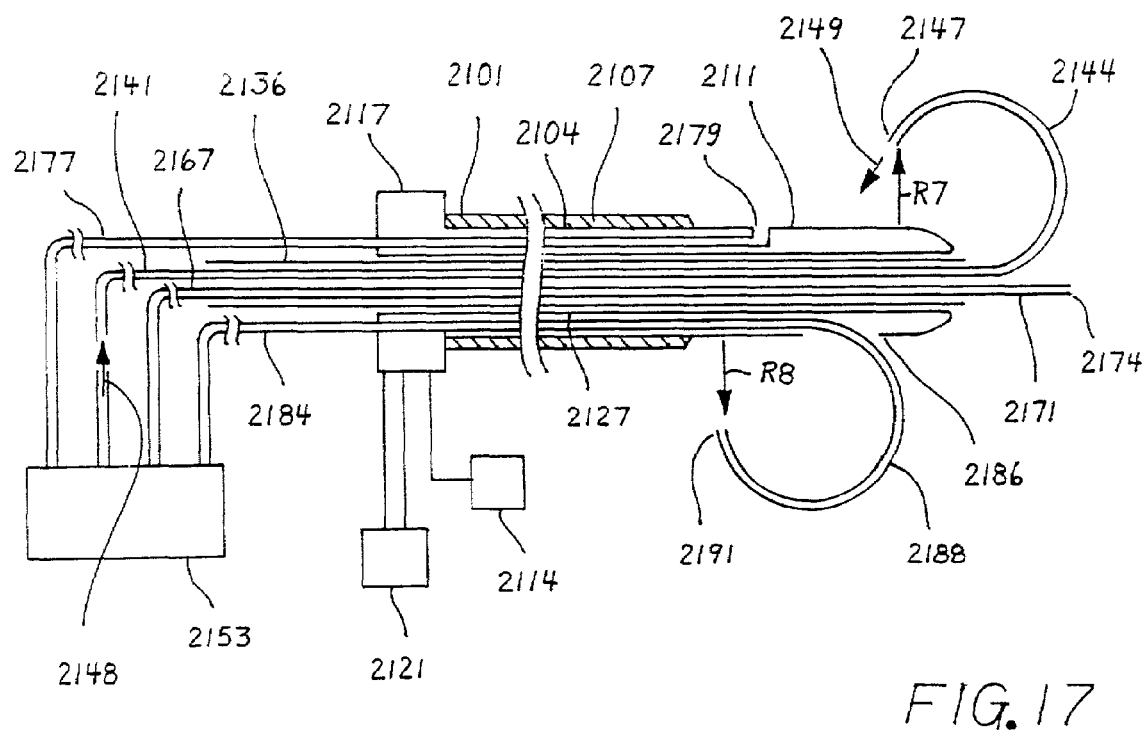
FIG. 17 is a schematic diagram showing a guide element-directed electrode having fluid injection ports.

Referring to FIG. 17, a guide element-directed electrode includes elongated member 2101 having tubular member 2104, which can be flexible or rigid. A portion of member 2101 has an insulated surface layer 2107. Exposed tip 2111 is at the distal portion of member 2101. Internal channel 2127, within member 2101, enables passage of member 2101 over a guide element that has already been inserted into the tissue. Tube 2136 is part of a guide element inside of channel 2127. Tube 2141 can move inside of tube 2136 and has a curved or off-axis distal portion 2144 that emerges from the distal end of tube 2136. Tube 2141 has an opening 2147 at its distal tip and is connected at its proximal end to a source 2153 of a fluid agent. The position R7 of opening 2147 relative to tip 2111 can be changed according to the depth of insertion of tube 2141 into tube 2136. Tube 2141 can be made, for example, from a nitinol or a steel tube which has a pre-curved shape at its distal portion 2144 so that when it emerges from tube 2136 it will move in a curved off-axis path. Tubes of different distal tip shapes can be selected to achieve different arc paths and tip locations R7. A fluid agent can be pumped out of source 2153, as indicated by arrow 2148, and into tube 2141 so that it emerges from opening 2147 as indicated by arrow 2149. For example, the tube 2141 can have a diameter of 0.1 to 1.0 millimeter and can be made from nitinol memory metal to achieve the precurved portion 2144.

Another tube 2167 can be passed inside guide element tube 2136 to enable the distal portion 2171 to emerge substantially straight out from electrode tip 2111. Another tube 2177 positioned inside of elongated member 2104 connects to an opening 2179 in tip 2111. A fluid agent can be pumped from source 2153 through 2177 and out of hole 2179 to fill space or infiltrate tissue near electrode tip 2111. Another tube 2184 passes within the elongated member 2104 and outside of tube 2136 and has a distal portion 2188 that emerges from the lateral portion of electrode tip 2111 through opening 2186. Distal portion 2188 has an arced shape and has an open end 2191 that is located at vector position R8 relative to tip 2111. The position R8 can be varied or selected by the degree of insertion of tube 2184 into member 2104. Injection of a fluid agent from pump 2153 out of open end 2191 will deposit the fluid agent at a desired position relative to tip 2111. A high frequency generator 2114 and electrode coolant supply 2121 can be connected to the electrode 2101 in a way similar to that described in connection with FIGS. 1, 3, and 4.

Referring to FIG. 17, guide element tube 2136 can be made from steel, nitinol, or plastic and have a range of diameters similar to those described in connection with foregoing figures. Tube 2136 can be a stainless steel or plastic tubing of diameter 0.5 to 1.5 millimeters according to the desired diameter of the elongated member 2104. The probe can include one or several injection tubes such as 2141 and 2167 that pass through tube 2136. The injection tubes can be made from metal or plastic. For example, tube 2141 can be made from a nitinol tubing which has a predetermined shape memory so that distal portion 2144 has a desired shape, radius of curvature, or deflection angle. Tube 2141 can be pulled back so that curved portion 2144 is withdrawn back into the distal portion of tube 2136. This can facilitate insertion of the guide tube 2136 into the tissue or into another component of a guidance system as, for example, illustrated by the FIGS. 1 and 2. For example, a guide needle or cannula can initially be inserted into the patient's tissue to establish a tract to a target. The guide tube can then be passed through the guide needle having the internal tubes withdrawn inside the guide tube. The guide needle can be withdrawn over guide tube and out of the patient's tissue leaving the guide tube in the tissue tract. Curved element 2144 can be sent out into the tissue to anchor the guide tube 2136 to the tissue. Elongated member 2101 can then be passed over guide tube 2136 so as to be positioned in the tissue tract with electrode tip 2111 adjacent to a target volume to be ablated. Curved element 2188 can be sent out into the tissue near tip 2111 to provide injection access or to further anchor tip 2111 to a target site. Tube 2184 can be a solid wire, such as nitinol or steel wire, with a preset curved position 2188 which is used for anchoring tip 2111 to tissue or to a vessel (such as an artery, vein, or natural cavity) near tip 2111. Element 2184 can be a tube containing a temperature sensor to monitor tissue temperature at position R8. Portions 2144 or 2188 can be electrically insulated or not insulated. For example, portion 2144 can be insulated so that it does not carry high frequency current into the tissue itself. Tube 2141 and portion 2144 can be uninsulated and connected to the high frequency source 2114 so that heating current will pass from curved portion 2144 into the tissue. Thus curved portion 2144 becomes part of the ablating electrode portion and can be used to influence the shape and size of the ablation volume.

Fluid agents can be injected into the tissue or space around the electrode tip 2111 to affect the process of heating and of destruction of tissue around tip 2111. For example, source 2153 can be a source of conductive fluid or gel such as saline or saline loaded gel. Injection of such a conductive fluid agent from tip openings 2147, 2174, or 2191 will alter the electrical conductivity of the volume near electrode tip 2111. For example, injection of conductive saline or gel around tip 2111 by appropriate positioning of tube openings 2147, 2174, or 2191 can reduce the impedance of current near tip 2111 and cause more power deposition and heating in tissue farther away from tip 2111. As a result, higher power can be delivered to the tissue-surrounding tip 2111 which results in a larger thermal ablation volume to be made. This is effective for ablation of larger tumors.

In another example, source 2153 can be a source of chemotherapeutic agent which when injected into tissue that is exposed to elevated temperatures can cause preferential death of cancerous cells compared to non-cancerous cells. For heat ablation with a high frequency electrode and without adjuvant chemotherapeutic exposure, the ablation volume is determined by the spatial region where temperatures reach 50° C. or greater. However, if in addition the chemotherapy agent is injected into the tissue, an increased volume of cancerous tissue death will occur as determined by the added spatial volume where temperatures reach between about 45 to 50° C. If no chemotherapy agent is injected into tissue, all cells, cancerous or non-cancerous, can be killed when exposed to temperatures above about 50° C. For example, when cells are exposed to chemotherapy agents, such as DOXIL, Doxilupisome, or liposomal doxorubicin, and also exposed to elevated temperatures, there will be a preferential death of cancerous cells as compared to non-cancerous cells for temperatures in the range of 45 to 50° C. Since the falloff of temperature versus radius from tip 2111 in FIG. 17 is slower at larger radii, this will mean that a substantially larger kill volume for cancerous cells or tumors will occur for high frequency heating combined with chemotherapy injection than for high frequency heating alone. Thus, injection of chemotherapy fluids into the target tissue volume near the electrode tip 2111 can advantageously increase the size of tumor volumes that can be killed with high frequency heating. The positions of ports such as 2147, 2174, or 2191 can be adjusted to infuse the chemotherapy fluid agent accurately and completely throughout the tumor volume without adjustment of the position of tip 2111. A further advantage is that the off-axis portions of the injection tubes such as 2144 or 2188 can anchor the electrode to the tissue and thus reduces the movement of tip 2111 relative to the target tissue during respiration, organ movement, or manipulation of the electrode or patient.

Figure 18:
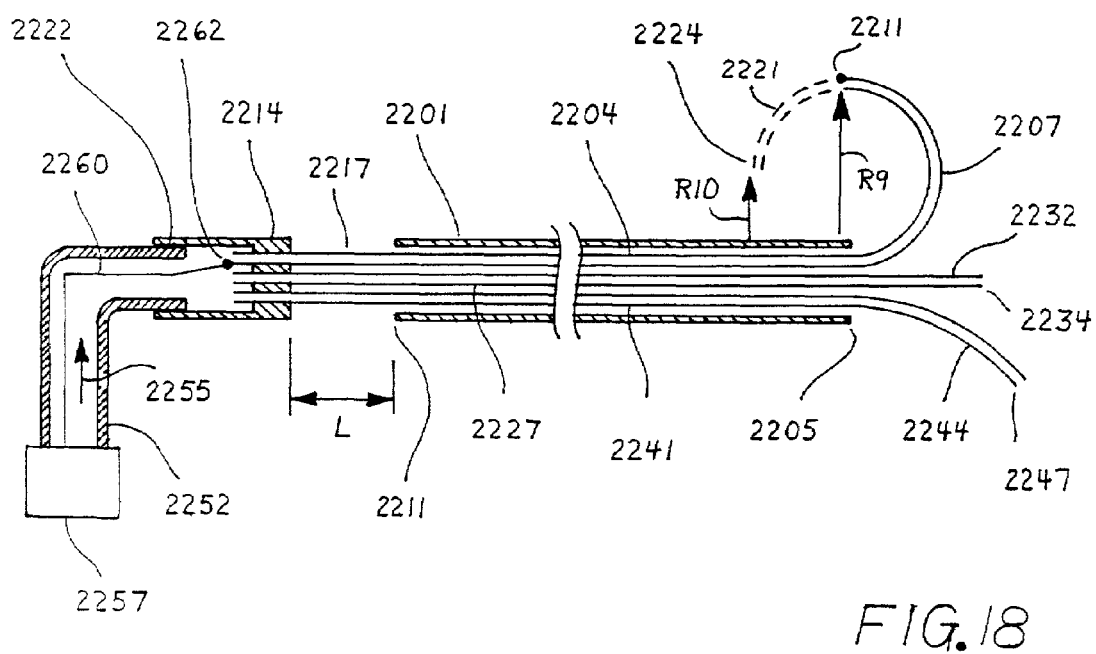
FIG. 18 is a schematic diagram showing a guide element with injection tubes.

Referring to FIG. 18, a guide element with extendable distal elements includes a sleeve 2201, which can be made from a metal or plastic tube or from a metal and plastic composite tube such as a metal wire wound or braided structure combined with a plastic coating or tubing. Sleeve 2201 can be flexible or non-flexible and can have outer diameter ranging, for example, from 0.1 to 2.0 millimeters or more depending on the geometry of the tissues or vessels into which it is placed. Inside of sleeve 2201 are one or more elements, such as element 2204 having a distal portion 2207 that can extend out of the distal opening 2205 of sleeve 2201. Element 2204 extends out of the proximal opening 2211 of sleeve 2201 and connects to hub 2214. Element 2204 can be moved within sleeve 2201 to retract the distal portion entirely or partially inside sleeve 2201. The degree of extension or retraction of portion 2207 from sleeve 2201, for example, can be gauged by the distance L of hub 2214 from proximal end 2211 or by the relation of index marks 2217 on element 2204 to distal end 2211. At one degree of extension, for example, the tip 2211 of portion 2207 is at position R9 relative to element 2201. When element 2204 is pushed deeper into 2201, the distal portion 2207 extends further, as illustrated by the dashed line 2221 so that the tip 2224 is now at distance R10 from 2201. Element 2204 can be a solid wire, and curved extension 2207 can provide an anchor to tissue near end 2205 which inhibits movement of the guide element relative to a target volume near distal end 2205. Alternatively, element 2204 can be a tube. Element 2204 can include a temperature sensor at tip 2211 to monitor tissue or heat ablation temperature at positions such as R9 or R10. Tip 2211 can be open so that an injectable agent such as saline, gel, chemotherapy agents, or CT, MRI, or X-ray radiographic agents can be injected through tubular element 2204 and be deposited into tissue near tip 2211.

Hub 2214 is attached to element 2204 and can be used by the operator to grip the element 2204 to move it in and out of sleeve 2201. The outer diameter of hub 2214 can be approximately equal to or less than the diameter of tube 2201 so that the inner guide channel of an electrode can slide over the entire guide element in FIG. 18. Hub 2214 can have a connection 2222 at its distal end for coupling to hose 2252 so that a fluid agent can be pumped from supply 2257 as indicated by arrow 2255. If element 2204 is a tube, the fluid will flow out of tip opening 2211. Connection 2260 can connect to element 2204 at junction 2262. Thus if the apparatus also includes, for example, a high frequency generator, impedance monitor, or stimulator, it can produce heat ablations from portion 2207, monitor impedance of tissue near 2207, or stimulate tissue near 2207. A stimulator can include an electronic apparatus to deliver pulses of current or voltage of selectable amplitude, width, and repetition rate that can produce a physiologically identifiable response when applied to tissue. Element 2204 or its distal portion 2207 can be a conductor that is uninsulated, and can be made, for example, from a nitinol or steel tube. This enables ablative heating from portion 2207. Alternatively, element 2204 and its distal portion 2207 can be insulated, as for example if they are made from a plastic tubing or from a metal (nitinol, steel, etc.) tubing or wire with an insulating coating such as a fluoropolymer (e.g., Teflon) or plastic. In that case, portion 2207 would not influence the ablative heating distribution from another electrode which can be active on an electrode structure passed over the guide element 2201.

Multiple extendable elements similar to element 2204 can be passed inside sleeve 2201 to anchor, heat ablate, or deliver fluid agents. A bundle of wire or tubular elements such as 2204, 2227, and 2241 can be clustered inside sleeve 2201, and they can move in and out of 2201 independently or in unison. The elements 2204, 2227, and 2241 have different shapes such as a circular arc or portion 2207, a curved off-axis extension such as portion 2247, or a straight projection such as portion 2232. Hub 2214 can be connected to all the elements 2204, 2227, and 2241 so that they can be extended in unison out of sleeve end 2205. Source 2257 can inject a fluid agent through all of the internal elements. Alternatively, elements 2204, 2227, and 2241 can move independently inside sleeve 2201. Individual hubs and fluid injection tubes from the supply 2257 (not shown) can connect to the individual internal elements so that independent anchoring of the elements to tissue and independent injection of fluid to target tissue can be achieved.

Figure 19:
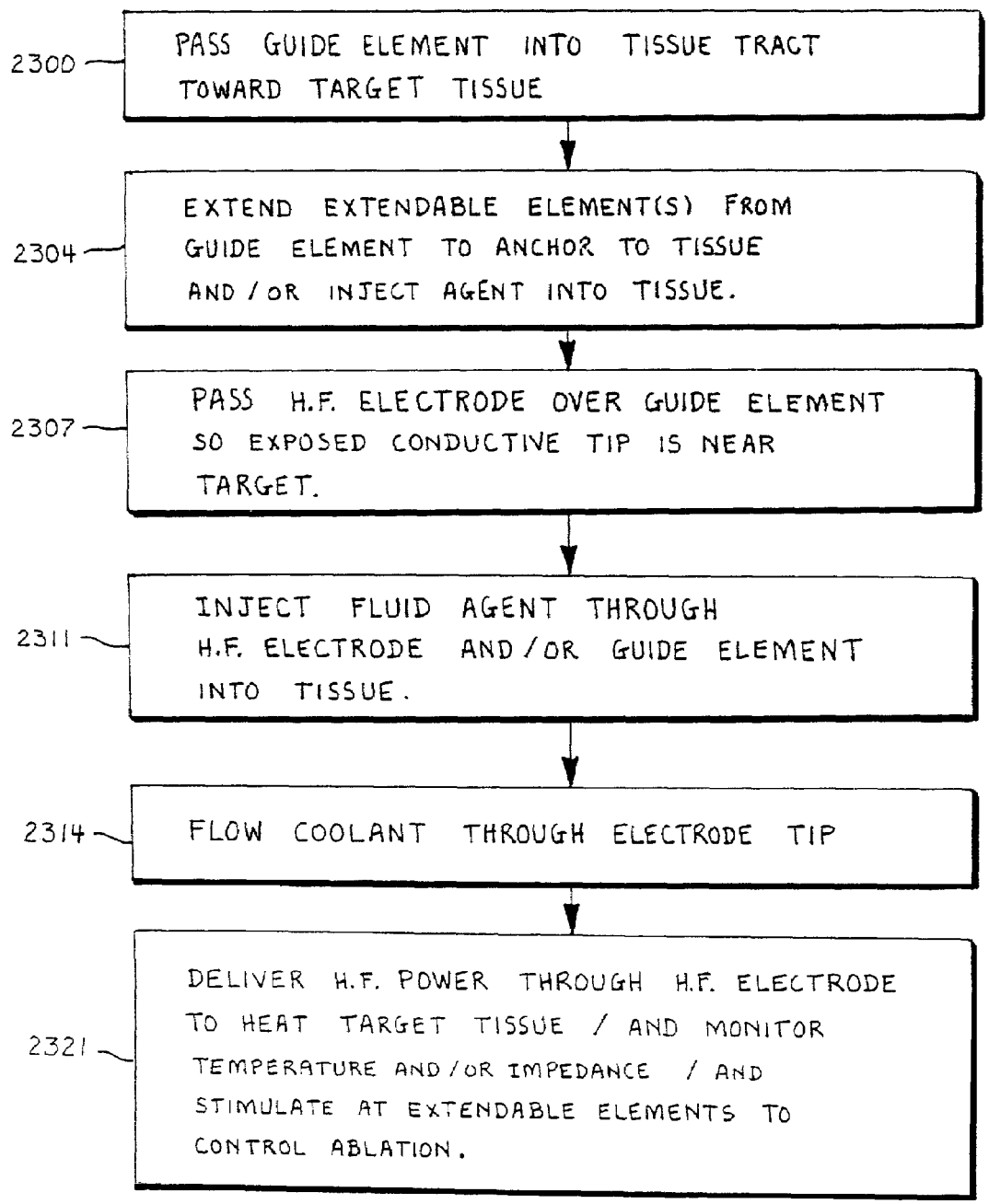
FIG. 19 is a flow chart showing a process employing a system including a guide element-directed electrode.

Referring to FIG. 19, a procedure is shown that relates to use of extendable elements from a guide element or from an electrode shaft. A guide element is passed along a tissue tract in the patient's body directed toward or into a target volume which, for example, can be a tumor (step 2300).

The extendable element or multiple extendable elements are extendable out of the distal portion of the guide element into the tissue (step 2304). The extendable elements or probes can be curved or straight probes made from wire or tubing. The step 2304 can include selecting extendable probes of known or desired radii and angles from the electrode tip. The step 2304 can include extending the probes to appropriate distances from the tip and selecting the appropriate agents to inject into the tissue for the clinician to enhance, modify, or enlarge the ablation or kill volume of tissue appropriate to clinician needs. Off-axis probes will anchor the guide element to proximate tissue. Step 2304 can include injecting a fluid agent such as saline, conductive gel, heat adjuvant chemotherapeutic agents, or imaging detectable agents for the purpose of modifying the electrical environment of the tissue, infusing chemotherapy agent into the tissue for enhanced destruction of tumors or cancerous cells, or injecting graphic marker agents in the tissue for location or relocation of a target position.

The next step is to pass a high frequency electrode having a guidance lumen over the guide element so that the tip of the electrode is near the target tissue to be ablated (step 2307).

The next step can be to inject a fluid or gel agent through the guide element or through the guide lumen of the electrode, or through extendable element included in the electrode, or through ports in the electrode wall (step 2311). This step 2311 can be as an alternative to agent injection in step 2304, or be in addition to the injection step in step 2304, or be eliminated if the injection in step 2304 is adequate for the clinical goals.

The next step is to flow coolant into the electrode to cool the electrode tip and thus to cool tissue around the tip (step 2314). This step can be eliminated if an ablation is made with a non-cooled electrode tip.

The next step is to connect the electrode to a high frequency generator and to deliver high frequency energy through the electrode tip to surrounding tissue (step 2321). The extendable elements can have temperature sensors in them, and this step can include monitoring temperatures in the tissue near the electrode tip during the ablation process. For example, if an ablation radius of 30 millimeters is desired, one of the extendable probes can be positioned in step 2304 so that its temperature sensor is 30 millimeters radius from the electrode tip. In step 2321, the high frequency power is raised to a sufficiently high level that the sensor temperature continues to read 50° C. for a set time such as 5 minutes, or 10 minutes or 20 minutes or more to be sure that all tissue within and up to the 30 millimeter radius is ablated. Multiple probes can be deployed and monitored simultaneously to control the profile and angular extent of the ablation volume.

A number of embodiments of the invention have been described. Nevertheless, it will be understood that various modifications may be made without departing from the spirit and scope of the invention. Accordingly, other embodiments are within the scope of the following claims.

What is claimed is:

1. A device for ablating tissue comprising:
a guide element;
a rigid elongate tubular member defining a longitudinally extending lumen having a distal opening and a proximal opening, the lumen dimensioned to pass along and over the guide element directed into the tissue, a distal portion of the tubular member having a blunt distal tip, the tubular member comprising a metal tube having an external surface and an electrical insulator configured to electrically insulate a portion of the external surface of the metal tube, an inner metal tube disposed within the metal tube and defining a portion of the lumen, the blunt tip comprising a fluid sealed junction between the metal tube and the inner metal tube;
an electrode disposed at a distal portion of the tubular member and configured to be energized with high frequency energy to thermally ablate the tissue; the electrode comprising an exposed portion of the external surface of the outer metal tube; and
a fluid channel within the tubular member, the fluid channel in fluid communication with a fluid input port and a fluid output port and in thermal communication with the electrode; the fluid channel being located at least in part between the metal tube and the inner metal tube.

2. The device of claim 1, wherein:
the tubular member comprises a plastic tube; and
the electrode comprises a metal element.

3. The device of claim 1, wherein the fluid output port is at a proximal portion of the elongate member.

4. The device of claim 1, wherein the fluid output port is at a proximal portion of the elongate member.

5. A system for ablation of tissue in the living body comprising:
a guide element; and
an ablation system including:
an elongate member defining a longitudinal channel having a distal opening and proximal opening, the elongate member being dimensioned to slide along and over the guide element directed into the tissue, a distal portion of the elongate member having a blunt distal tip, the elongate member comprising a metal tube having an external surface and an electrical insulator configured to electrically insulate a portion of the external surface of the metal tube, an inner metal tube disposed within the metal tube and defining a portion of the channel, and the blunt tip comprising a fluid sealed junction between the metal tube and the inner metal tube; and
an electrode at a distal portion of the elongate member and configured to be energized with high frequency energy to ablate the tissue; the electrode comprising an exposed portion of the external surface of the outer metal tube;
a fluid channel within the elongate member the fluid channel in fluid communication with a fluid input port and a fluid output port and in thermal communication with the electrode; the fluid channel being located at least in part between the metal tube and the inner metal tube.

6. The system of claim 1 wherein the guide element comprises a flexible guide wire.

7. The system of claim 5 wherein the guide element comprises a rigid stylet wire.

8. The system of claim 5 wherein the guide element comprises an anchor that extends laterally from a distal guide portion of the guide element, the anchor configured to anchor the distal guide portion near a target.

9. The system of claim 5 wherein the guide element comprises a tube containing a movable member.

10. The system of claim 9 wherein the movable member is a tube.

11. The system of claim 9 wherein the movable member is an anchor.

12. The system of claim 5 wherein the ablation system further comprises:
 a high frequency generator; and
 electrical conductors connecting the high frequency generator to the electrode.

13. The system of claim 5 wherein:
 the ablation system further comprises a coolant supply connected to the fluid input.

14. The system of claim 5 wherein the ablation system further comprises a fluid agent injector.

15. The system of claim 5, wherein the fluid output port is at a proximal portion of the elongate member.

16. A method for thermal ablation of a target volume comprising:
 perforating and penetrating a living body using a guide element to establish a tract through the body to the target volume by at least passing a sharp needle through skin and tissue;
 sliding an electrode along and over the guide element directed into the body to position the electrode near the target volume, the electrode including an elongate member defining a longitudinal passage dimensioned to pass along the guide wire, a conductive surface at a distal portion of the elongate member, and an electrical connection between the conductive surface and a proximal portion of the elongate member, by at least passing the guide wire through the needle and removing the needle over the guide wire to leave the guide wire in the tract;
 connecting the electrical connection to a high frequency generator;
 supplying high frequency energy from the generator through the electrode to the target volume to thermally ablate the target volume.

17. The method of claim 16 wherein positioning comprises deploying an anchor from the guide wire to anchor the guide wire in the tract.

18. The method of claim 16 further including dilating the tissue along the tract after positioning the guide wire by passing a dilating element over the guide wire to expand the tissue along the tract prior to sliding the electrode along the guide wire.

19. The method of claim 16 further comprising introducing a fluid agent through the guide element.

20. The method of claim 16 further comprising introducing a chemotherapeutic agent through the guide element prior to or while supplying high frequency energy.

21. A method for thermal ablation of a target volume comprising:
 perforating and penetrating a living body using a guide element to establish a tract through the body to the target volume;
 sliding an electrode along and over the guide element directed into the body to position the electrode near the target volume, the electrode including an elongate member defining a longitudinal passage dimensioned to pass along the guide wire, a conductive surface at a distal portion of the elongate member, and an electrical connection between the conductive surface and a proximal portion of the elongate member;
 connecting the electrical connection to a high frequency generator;
 supplying high frequency energy from the generator through the electrode to the target volume to thermally ablate the target volume; and
 introducing a chemotherapeutic agent through the guide element prior to or while supplying high frequency energy.

22. The device of claim 1, wherein the blunt distal tip is a conical tip.

23. The system of claim 5, wherein the blunt distal tip is a conical tip.

24. The device of claim 1, wherein the blunt distal tip is fluidly sealed to the tubular member and the inner metal tube.

* * * * *

UNITED STATES PATENT AND TRADEMARK OFFICE
CERTIFICATE OF CORRECTION

PATENT NO. : 7,077,842 B1
APPLICATION NO. : 10/058967
DATED : January 30, 2002
INVENTOR(S) : Eric R. Cosman It is certified that error appears in the above-identified patent and that said Letters Patent is hereby corrected as shown below:

On the Title Page (76) of the Patent, the Inventor should read
--Eric R. Cosman, 872 Concord Ave., Belmont, MA (US) 02478-0002
 Eric R. Cosman, Jr., 872 Concord Ave., Belmont, MA (US) 02478-0002--

Signed and Sealed this

Twenty-fifth Day of March, 2008

JON W. DUDAS
*Director of the United States Patent and Trademark Office*